US012746002B2

(12) United States Patent
Rotem et al.

(10) Patent No.: US 12,746,002 B2
(45) Date of Patent: Sep. 29, 2026

(54) SURGICAL KNOT PUSHER

(71) Applicant: NOVELRAD LTD., Kibbutz Metzer (IL)

(72) Inventors: Shachar Rotem, Kibbutz Metzer (IL); Ori Goldor, Amikam (IL); Netanel Sharabani, Rishpon (IL); Tomer Katz, Kfar Glikson (IL)

(73) Assignee: NOVELRAD LTD., Kibbutz Metzer (IL)

( * ) Notice: Subject to any disclaimer, the term of this patent is extended or adjusted under 35 U.S.C. 154(b) by 16 days.

(21) Appl. No.: 19/107,573

(22) PCT Filed: Aug. 29, 2023

(86) PCT No.: PCT/IB2023/058531
§ 371 (c)(1),
(2) Date: Feb. 27, 2025

(87) PCT Pub. No.: WO2024/047525
PCT Pub. Date: Mar. 7, 2024

(65) Prior Publication Data
US 2025/0241637 A1 Jul. 31, 2025

Related U.S. Application Data

(60) Provisional application No. 63/401,744, filed on Aug. 29, 2022.

(51) Int. Cl.
*A61B 17/04* (2006.01)

(52) U.S. Cl.
CPC ...... *A61B 17/0469* (2013.01); *A61B 17/0467* (2013.01); *A61B 2017/0474* (2013.01)

(58) Field of Classification Search
CPC ........ A61B 2017/0474; A61B 17/0469; A61B 17/0467; A61B 2017/0496; A61B 17/04; A61B 17/0482; A61B 2017/2946
See application file for complete search history.

(56) References Cited

U.S. PATENT DOCUMENTS 5,324,298 A 6/1994 Phillips et al.
5,423,837 A 6/1995 Mericle et al.
(Continued)

FOREIGN PATENT DOCUMENTS

KR 101765653 B1 8/2017
WO 2017025971 A1 2/2017

OTHER PUBLICATIONS

PCT International Search Report and Written Opinion for International Application No. PCT/IB2023/058531, mailed Nov. 22, 2023, 12pp.

*Primary Examiner* — Katherine M Shi
(74) *Attorney, Agent, or Firm* — The Roy Gross Law Firm, LLC; Roy D. Gross

(57) ABSTRACT

A knot pusher (10) includes a tubular suture holder (12) having a tubular wall with a suture-receiving slot (20), within which a mandrel (22) is axially displaceable. The suture-receiving slot (20) preferably includes a narrow distal slot portion, a first transition region starting at a first distance from the distal tip at which a first edge (26) is shaped so as to diverge from a second edge (28) of the slot while the second edge extends in an axial direction, and a second transition region, starting further from the distal tip, at which the second edge diverges from the axial direction away from the first edge. This defines an oblique groove crossing the tubular suture holder for receiving a suture.

10 Claims, 22 Drawing Sheets

(56) References Cited

U.S. PATENT DOCUMENTS

| | | | |
|---|---|---|---|
| 5,797,929 | A | 8/1998 | Andreas et al. |
| 2017/0319199 | A1 | 11/2017 | Nobles et al. |
| 2020/0405288 | A1 | 12/2020 | George et al. |

FIG. 1A
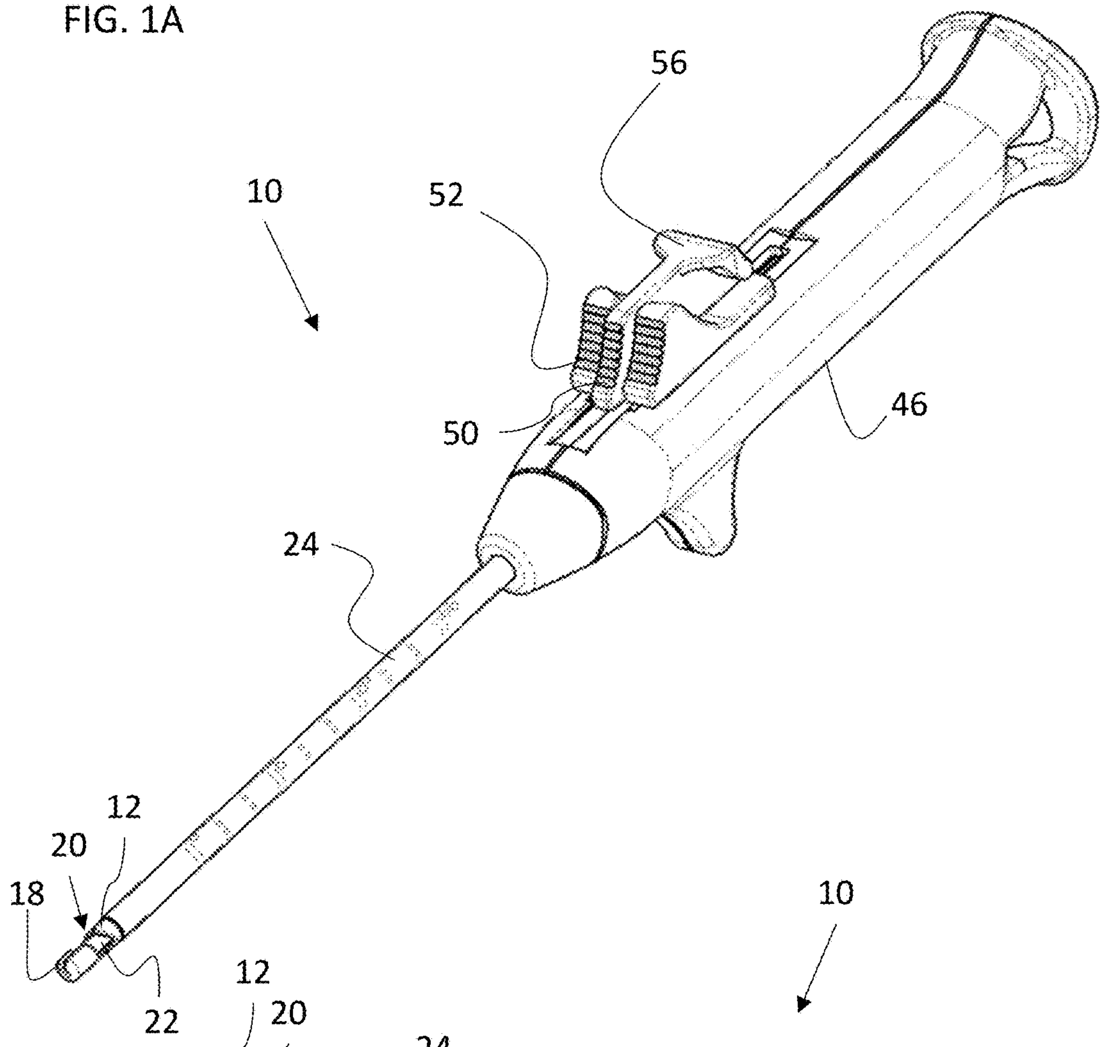
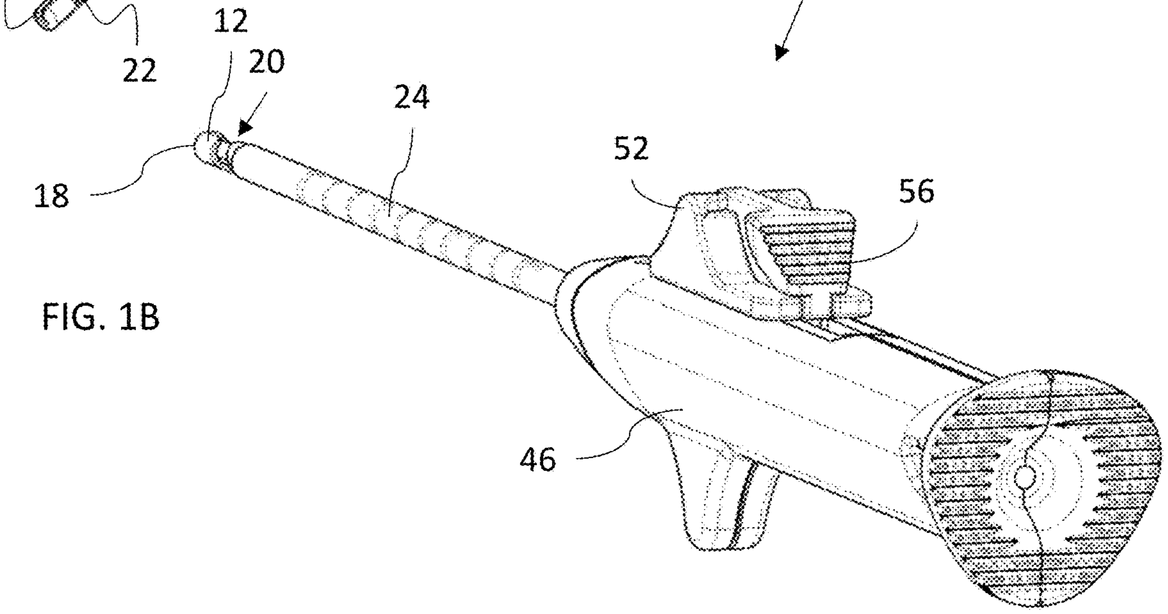
FIG. 1B

Open SG state

Closed SG state

SURGICAL KNOT PUSHER

FIELD AND BACKGROUND OF THE INVENTION

The present invention relates to surgical devices and, in particular, it concerns a device for use in pushing and tightening knots in sutures.

Many surgical techniques employ sutures which must be tied. In many cases, this is done by employing a knot pusher to advance a sliding knot along one side of the suture, referred to as the "rail thread." Once in place, the knot is converted to a locked knot by additional tension applied to another thread, referred to as the "locking thread."

SUMMARY OF THE INVENTION

The present invention is a knot pusher.

According to the teachings of an embodiment of the present invention there is provided, a knot pusher for pushing a knot along a suture, the knot pusher comprising: (a) a tubular suture holder having a tubular wall defining an internal bore having a central longitudinal axis and terminating at a distal tip, the tubular suture holder having a suture-receiving slot formed through the tubular wall and extending proximally from the distal tip so that a segment of a suture can be loaded via the suture-receiving slot into the internal bore with a continuation of the suture emerging from the distal tip; and (b) a mandrel axially displaceable within the internal bore, the mandrel biased from a retracted position, in which the suture-receiving slot allows loading of a segment of a suture via the suture-receiving slot into the internal bore with a continuation of the suture emerging from the distal tip, towards an advanced position in which the mandrel obstructs a distal portion of the suture-receiving slot so as to entrap the segment of the suture within a part of the internal bore with the continuations of the suture extending from the distal tip and from a proximal portion of the suture-receiving slot, the mandrel defining a channel within the part of the internal bore so as to allow sliding of the suture along the channel, wherein the suture-receiving slot includes: (i) a distal slot portion, adjacent to the distal tip, formed with a first edge and a second edge separated by a first width, the first width subtending an angle to the central longitudinal axis of less than 30 degrees, (ii) a first transition region starting at a first distance from the distal tip at which the first edge is shaped so as to diverge from the second edge and the second edge extends in an axial direction, and (iii) a second transition region starting at a second distance from the distal tip, the second distance being greater than the first distance, at which the second edge diverges from the axial direction away from the first edge, the first edge in the first transition region and the second edge in the second transition region defining at least part of an oblique groove crossing the tubular wall for receiving a suture.

According to a further feature of an embodiment of the present invention, the oblique groove corresponds to an opening through the tubular wall the angular extremities of which subtend a groove angle of between 120 degrees and 240 degrees about the central longitudinal axis, and wherein an angular position of the distal slot portion is angularly spaced away from the ends of the oblique groove by at least about 20 degrees.

According to a further feature of an embodiment of the present invention, a maximum depth of the oblique groove defines a base line of the oblique groove, and wherein a base plane of the oblique groove is defined as a plane containing the base line and parallel to the central axis, the second edge at a beginning of the second transition region providing a suture-capturing prominence, the suture-capturing prominence being at a height X from the base plane, where X is larger than the first width.

According to a further feature of an embodiment of the present invention, height X is at least 30% of a radius of the tubular wall of the tubular suture holder.

According to a further feature of an embodiment of the present invention, the distal tip of the tubular suture holder is formed with an end closure closing a majority of an area of the internal bore, the end closure including a radial slot contiguous with the distal slot portion of the suture-receiving slot, the radial slot terminating at a retaining aperture having a lateral dimension that is greater than the first width.

According to a further feature of an embodiment of the present invention, the mandrel terminates in a least one projecting finger, the projecting finger having a cross-sectional area that is less than half of a cross-sectional area of the mandrel proximal to the projecting finger, the projecting finger being deployed such that, when a suture is trapped by the mandrel in the suture-receiving slot, tension in the suture tending to retract the mandrel towards the retracted position engages the suture with the projecting finger so as to inhibit release of the suture and to apply force to the suture to return the suture towards the distal tip.

According to a further feature of an embodiment of the present invention, there is also provided an axially-displaceable cutting element, external or internal to the tubular suture holder, and selectively displaceable in a distal direction to cut a suture exiting via a proximal portion of the suture-receiving slot.

According to a further feature of an embodiment of the present invention, there is also provided a handle supporting the tubular suture holder, the handle having a manually operable slider arrangement and an associated spring arrangement including at least one spring, the manually operable slider arrangement configured such that an axial force applied to the slider arrangement in a first axial direction acts against the spring arrangement to displace the mandrel from the advanced position to the retracted position and an axial force applied to the slider arrangement in a second axial direction opposite to the first axial direction acts against the spring arrangement to displace the cutting element to cut a suture exiting via a proximal portion of the suture-receiving slot, wherein the slider arrangement is locked by a locking configuration against displacement in the first axial direction, and wherein a release element of the slider arrangement is configured such that an initial displacement of the release element in the first axial direction is effective to unlock the locking configuration prior to displacement of the mandrel.

There is also provided according to the teachings of an embodiment of the present invention, a knot pusher for pushing a knot along a suture, the knot pusher comprising: (a) a tubular suture holder having a tubular wall defining an internal bore having a central longitudinal axis and terminating at a distal tip, the tubular suture holder having a suture-receiving slot formed through the tubular wall and extending proximally from the distal tip, the suture-receiving slot including a distal slot portion, adjacent to the distal tip, formed with a first edge and a second edge separated by a first width, and an oblique groove, proximal to and contiguous with the distal slot portion, having a width greater than the first width, for receiving a suture; and (b) a mandrel axially displaceable within the internal bore, the mandrel biased to an advanced position in which the mandrel obstructs a distal portion of the suture-receiving slot so as to slidingly-entrap a suture entering the internal bore at the distal tip and exiting via the oblique groove, the mandrel being retractable to a retracted position in which the suture-receiving slot is open to receive a suture, wherein the mandrel terminates in a least one projecting finger, the projecting finger having a cross-sectional area that is less than half of a cross-sectional area of the mandrel proximal to the projecting finger, the projecting finger being deployed such that, when a suture is trapped by the mandrel in the suture-receiving slot, tension in the suture tending to retract the mandrel towards the retracted position engages the suture with the projecting finger so as to inhibit release of the suture and to apply force to the suture to return the suture towards the distal tip.

There is also provided according to the teachings of an embodiment of the present invention, a knot pusher for pushing a knot along a suture, the knot pusher comprising: (a) a tubular suture holder having a tubular wall defining an internal bore having a central longitudinal axis and terminating at a distal tip, the tubular suture holder having a suture-receiving slot formed through the tubular wall and extending proximally from the distal tip, the suture-receiving slot including a distal slot portion, adjacent to the distal tip, formed with a first edge and a second edge separated by a first width, and an oblique groove, proximal to and contiguous with the distal slot portion, having a width greater than the first width, for receiving a suture; (b) a mandrel axially displaceable within the internal bore, the mandrel biased to an advanced position in which the mandrel obstructs a distal portion of the suture-receiving slot so as to slidingly-entrap a suture entering the internal bore at the distal tip and exiting via the oblique groove, the mandrel being retractable to a retracted position in which the suture-receiving slot is open to receive a suture; (c) an axially-displaceable cutting element, external or internal to the tubular suture holder, and selectively displaceable in a distal direction to cut a suture exiting via a proximal portion of the suture-receiving slot; and (d) a handle supporting the tubular suture holder, the handle having a manually operable slider arrangement and an associated spring arrangement including at least one spring, the manually operable slider arrangement configured such that an axial force applied to the slider arrangement in a first axial direction acts against the spring arrangement to displace the mandrel from the advanced position to the retracted position and an axial force applied to the slider arrangement in a second axial direction opposite to the first axial direction acts against the spring arrangement to displace the cutting element to cut a suture exiting via a proximal portion of the suture-receiving slot, wherein the slider arrangement is locked by a locking configuration against displacement in the first axial direction, and wherein a release element of the slider arrangement is linked to the locking configuration such that an initial displacement of the release element in the first axial direction is effective to unlock the locking configuration prior to displacement of the mandrel.

BRIEF DESCRIPTION OF THE DRAWINGS

The invention is herein described, by way of example only, with reference to the accompanying drawings, wherein:

FIGS. 1A and 1B are front and rear isometric views, respectively, of a knot pusher and suture cutter, constructed and operative according to an embodiment of the present invention;

DESCRIPTION OF THE PREFERRED EMBODIMENTS

Figure 2A:
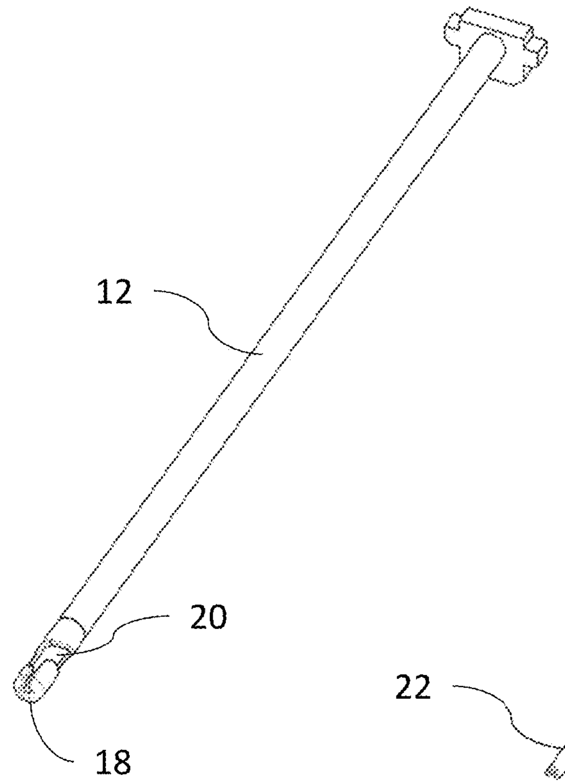
FIGS. 2A-2C are isometric views of a tubular suture holder, a mandrel assembly and a cutting element, respectively, from the knot pusher and suture cutter of FIG. 1A.
Figure 2B:
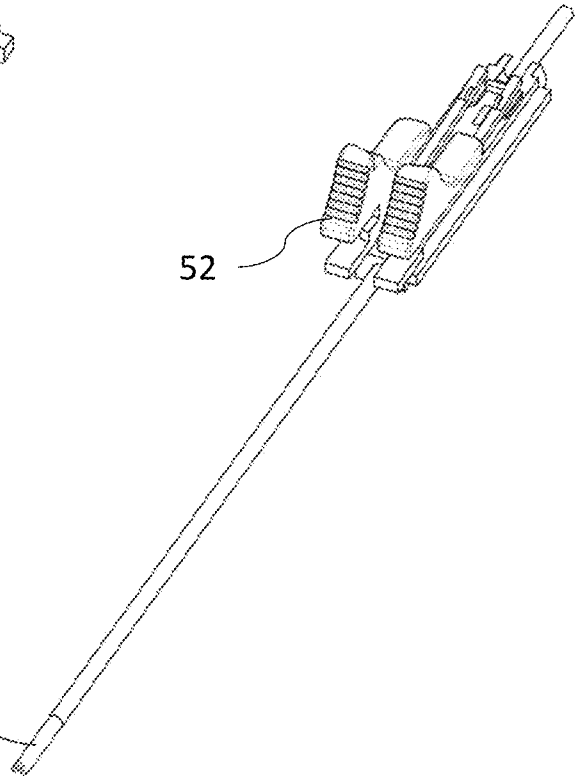

The present invention is a knot pusher for pushing a knot along a suture, preferably integrated with a suture cutter.

The principles and operation of knot pushers according to the present invention may be better understood with reference to the drawings and the accompanying description.

Referring now to the drawings, FIGS. 1A-25D illustrate a knot pusher, generally designated 10 or 10', constructed and operative according to various embodiments of the present invention, for pushing a knot along a suture.

In general terms, referring collectively to all the variants illustrated, knot pusher 10 includes a tubular suture holder 12 having a tubular wall defining an internal bore 14 having a central longitudinal axis 16 and terminating at a distal tip 18. Tubular suture holder 12 has a suture-receiving slot 20, formed through the tubular wall, that extends proximally from distal tip 18. A mandrel 22 is displaceable within internal bore 14 between a closed position (best seen in FIGS. 7C, 10B and 16A) in which mandrel 22 obstructs a distal portion of the suture-receiving slot 20 so as to slidingly-entrap a segment of a suture 100 within the internal bore so that the continuation of the suture emerges from distal tip 18 and from a proximal portion of suture-receiving slot 20, and an open position (best seen in FIGS. 7A, 7B and 16C) in which the suture-receiving slot 20 is open for loading of a segment of the suture 100. Suture-receiving slot 20 together with mandrel 22 are referred to herein as a "suture gate" (SG), which is opened or closed according to the corresponding position of mandrel 22. The displacement of mandrel 22 is typically axial, where the mandrel is biased towards an advanced (distal) closed position and is selectively retractable to a retracted (proximal) open position, although certain aspects of the present invention are also applicable to mandrels which undergo a rotary motion or any other more complex motion between the open and closed positions.

Figure 5A:
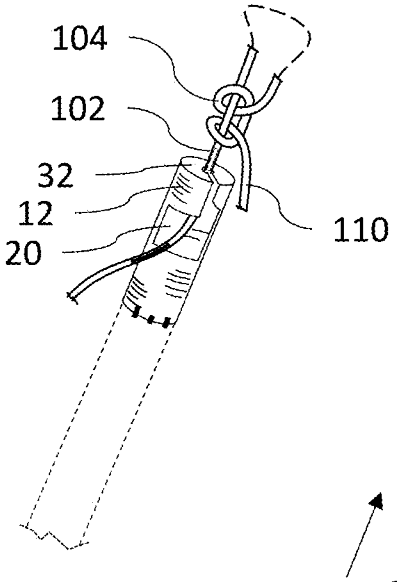
FIG. 5A is a schematic illustration of the knot pusher of FIG. 1A being employed to push a sliding knot along a rail thread during fastening of a suture.
Figure 5B:
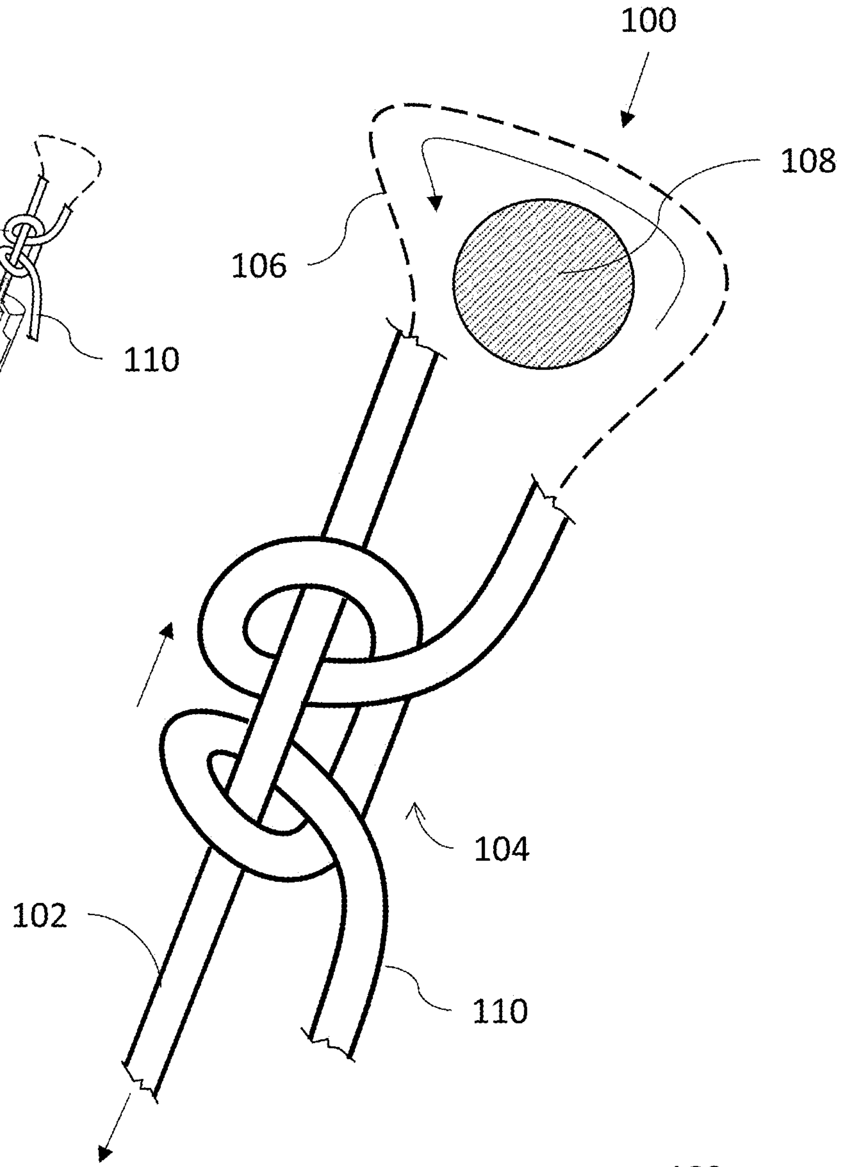
FIGS. 5B and 5C are schematic enlarged illustrations of the form of the sliding knot during pushing and after locking, respectively.
Figure 5C:
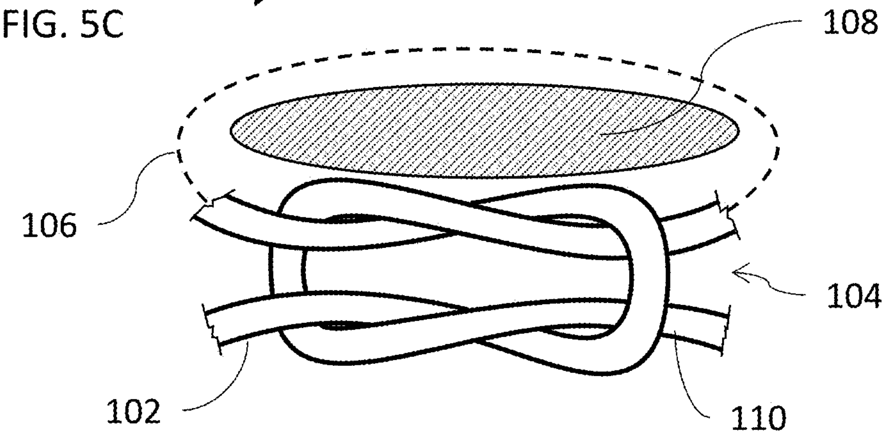
Figure 7A:
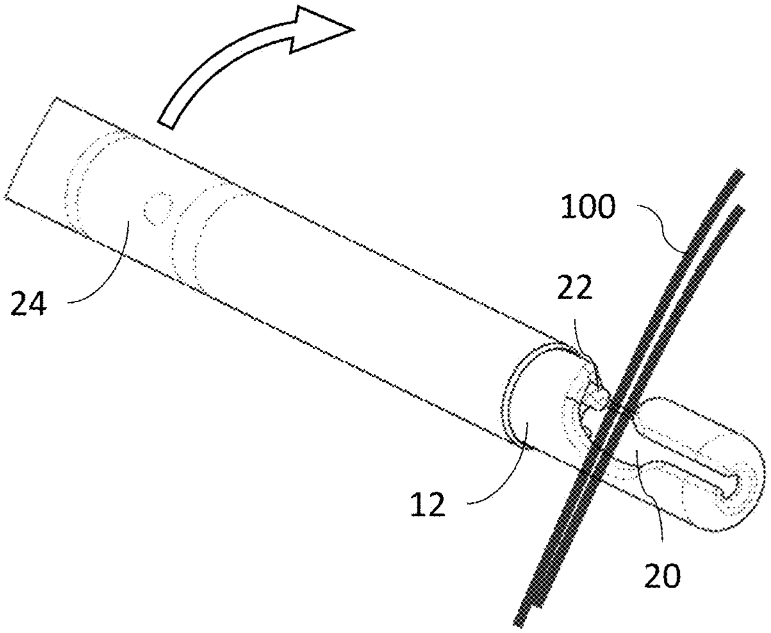
FIGS. 7A-7C are isometric views showing stages of loading sutures into the knot pusher of FIG. 1A.
Figure 7B:
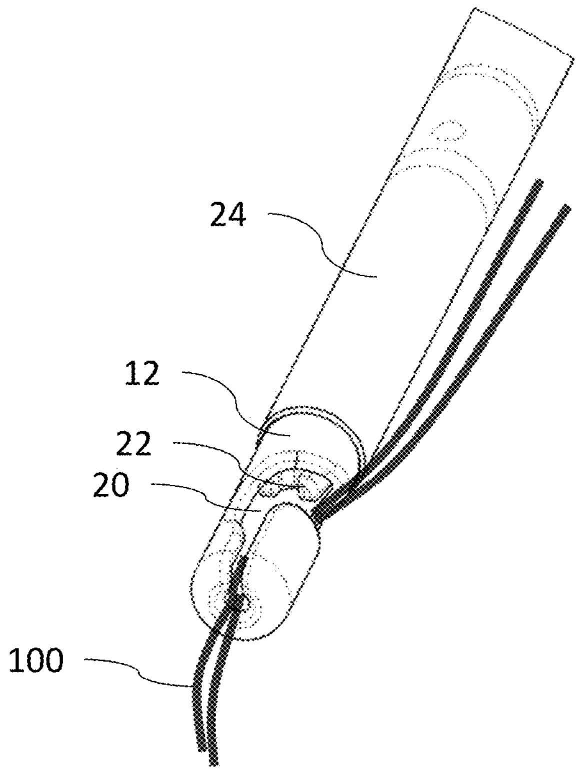
Figure 7C:
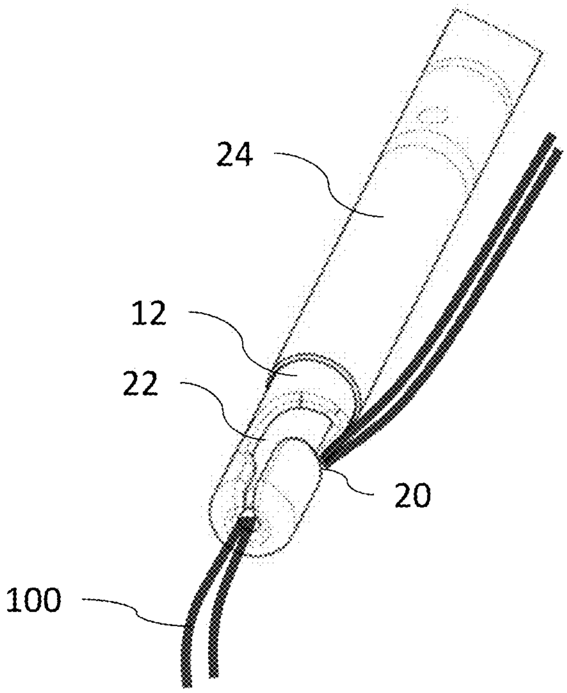
Figure 8:
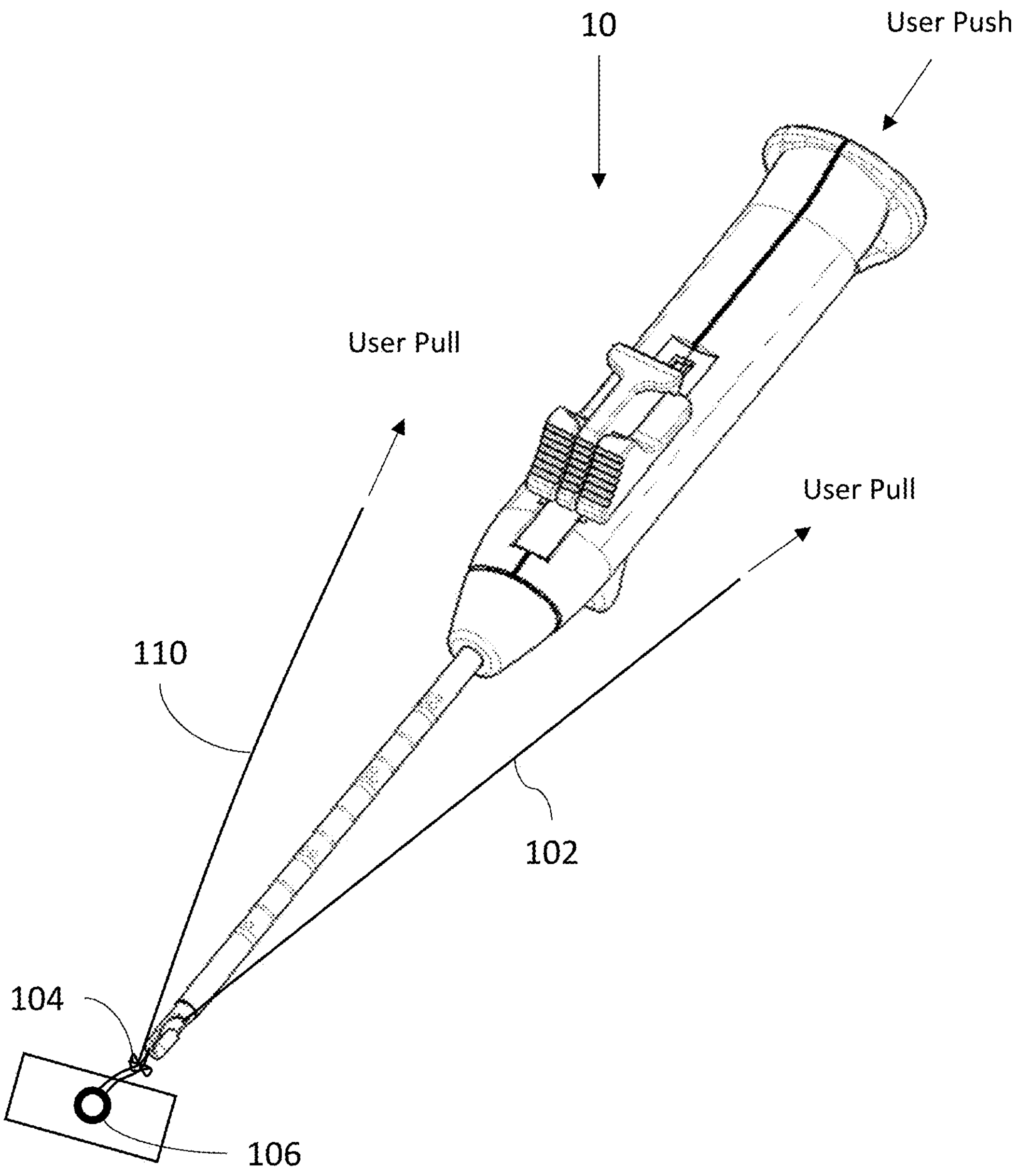
FIG. 8 is an isometric view illustrating the forces preferably applied by a user during tightening of a knot during a surgical procedure.
Figure 9A:
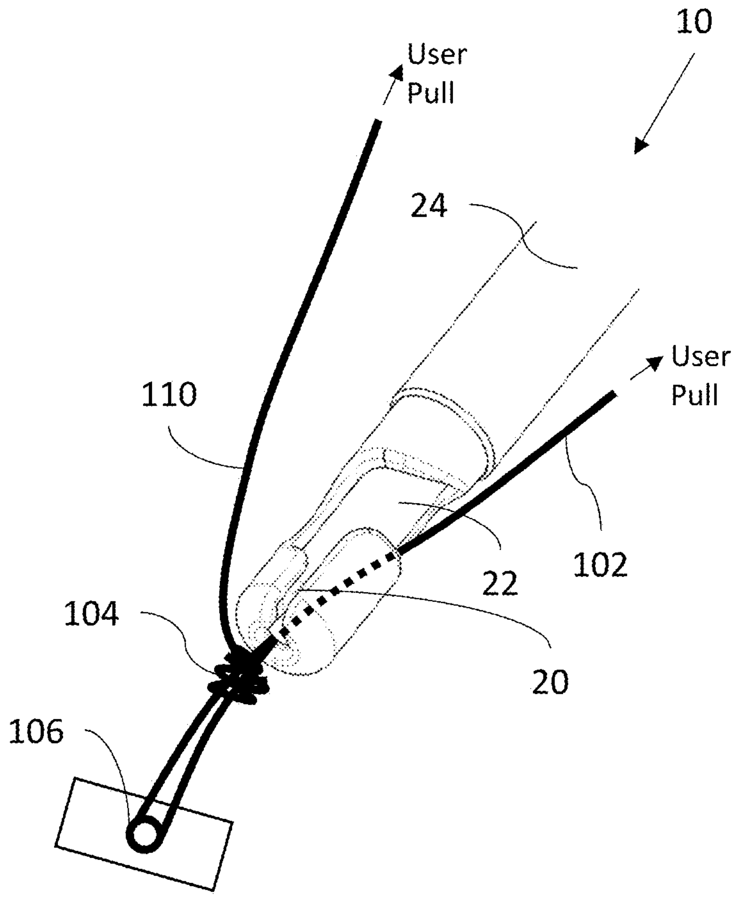
FIG. 9A is an enlarged view of a distal tip of the knot pusher in the state of FIG. 8.
Figure 9B:
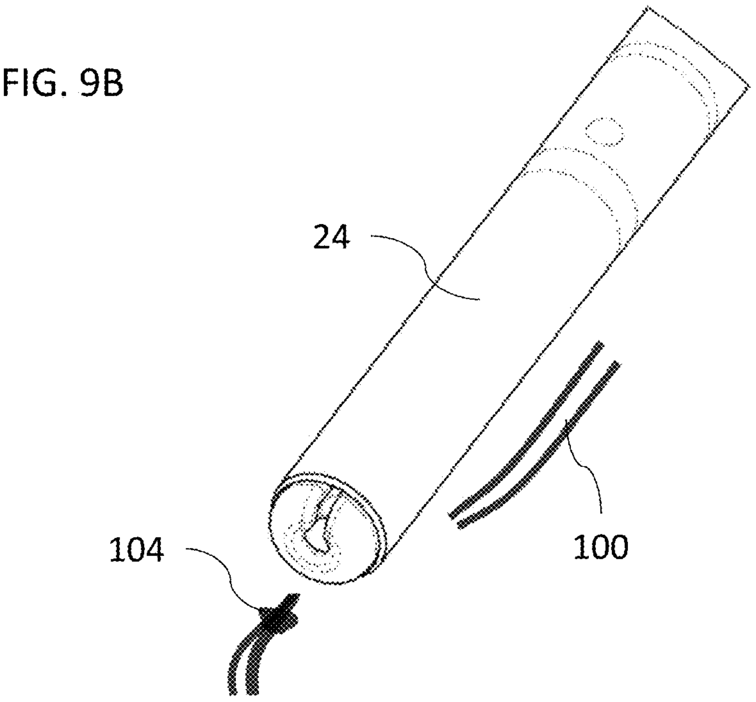
FIG. 9B is a view similar to FIG. 9A during operation of a suture cutter element.

The general operation and function of knot pusher 10 is typically as follows. With the mandrel 22 retracted, a segment of one or more suture is loaded into suture-receiving slot 20 (for example, through a sequence to be described in more detail below) so as to lie within a part of internal bore 14 from a proximal region of slot 20 to the distal tip 18 of tubular suture holder 12, as illustrated in FIG. 7B. Mandrel 22 is then displaced to its closed position, closing the suture gate so as to trap the suture. Mandrel 22 is shaped so as to define a channel within the part of internal bore 14 as best seen in FIG. 10B, so as to allow sliding of suture 100 along said internal bore or, in other language, to allow the knot pusher to be slid along the suture. The knot pusher can thus be used as illustrated in FIGS. 5A-5C, 8 and 9A to engage and advance along one or more rail thread 102 so as to push a sliding knot (sliding hitch) 104 along the rail thread while tension is applied to the rail thread, thereby tightening a loop 106 that performs whatever function the suture is intended to perform (e.g., holding two regions of tissue together or tightening around some object 108). Once the loop is suitably tightened, additional tension applied to a locking thread 110 (while rail thread 102 is maintained under tension) converts the form of the sliding knot to a locked knot (FIG. 5C). Where multiple knots are required, further knots can be formed and tightened using the knot pusher. Finally, in particularly preferred cases where the knot pusher also includes a cutting element 24, the rail thread(s) 102 are released by opening the suture gate, and all of the suture threads are reloaded into the suture gate. The knot pusher is then slid down the sutures to the desired location for cutting, and the cutting element is actuated (as described further below) to cut the sutures above the knot (FIG. 9B).

Various aspects of the present invention provide further elaborations on the particular structures and functions described above. A first aspect of the present invention provides particularly advantageous forms of suture-receiving slot 20, while a second aspect of the present invention provides particularly advantageous forms of mandrel 22. A third aspect of the present invention provides a handle with a particularly preferred implementation of a user interface for operating the knot pusher. A fourth aspect of the present invention relates to a knot pusher configuration that can be used over-the-wire (OTW) in applications in which there is a guidewire in place that can be used to direct the device to the location where knots are to be tightened. Each of these aspects of the invention can be used to advantage alone, with implementations of a knot pusher which vary materially from the other aspects of the invention described herein. However, some or all of these various aspects of the invention are believed to be particularly suited to implementation in a single device to provide a particularly advantageous combination of features, as will be described below.

Figure 3A:
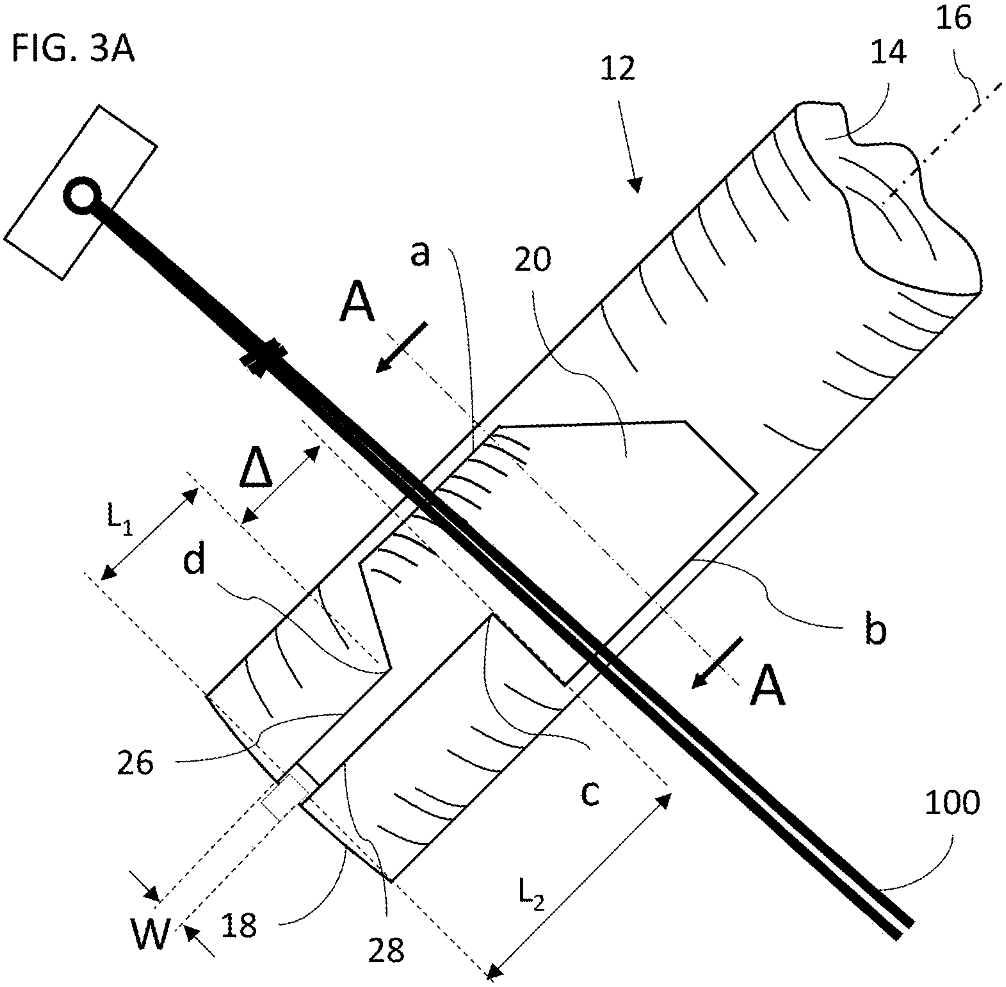
FIG. 3A is a schematic illustration of a distal part of the tubular suture holder of FIG. 2A illustrating a form of a suture-receiving slot according to an embodiment of one aspect of the present invention.
Figure 6A:
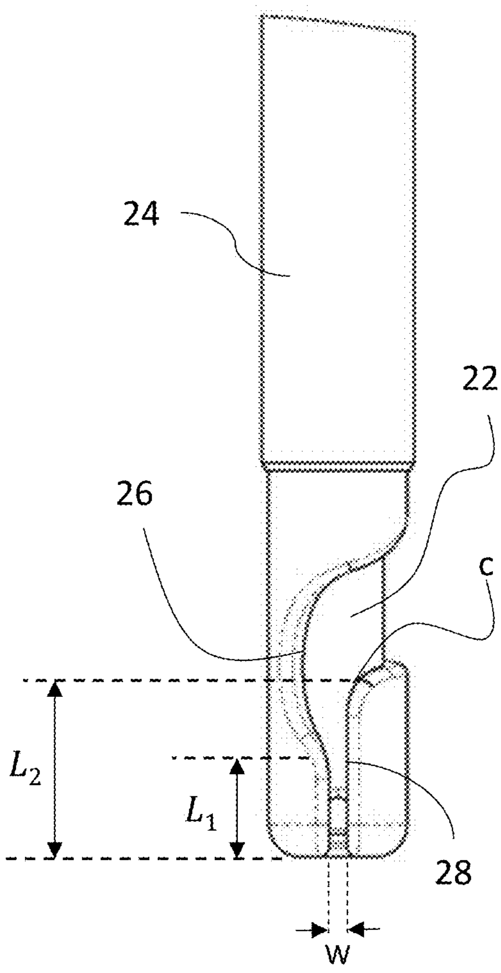
FIGS. 6A and 6B are side views of two implementations of the suture-receiving slot.
Figure 6B:
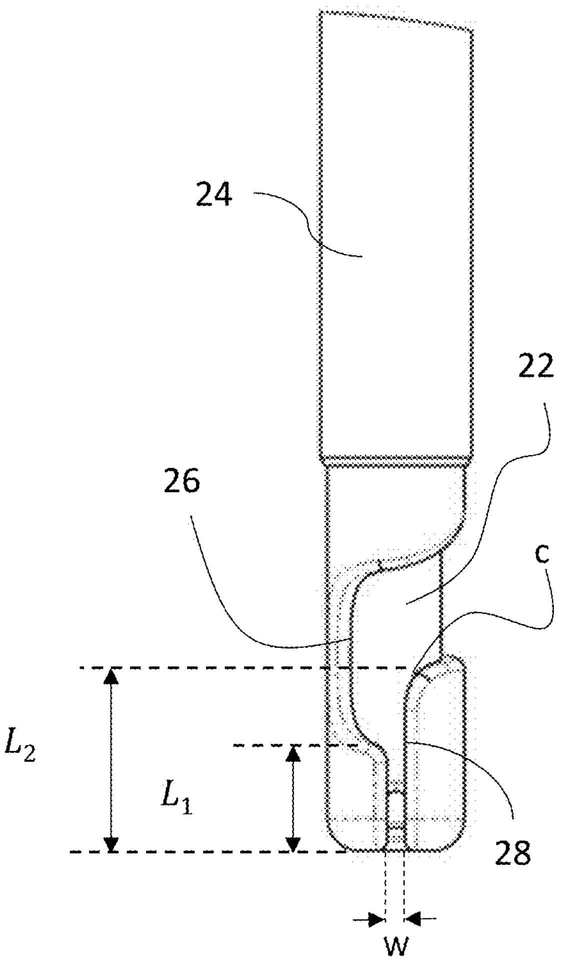

Turning now to the preferred form of suture-receiving slot 20, this is illustrated schematically in FIG. 3A, and in non-limiting preferred exemplary embodiments in FIGS. 6A and 6B. The slot preferably includes a distal slot portion, adjacent to distal tip 18, formed with a first edge 26 and a second edge 28 separated by a first width W. The first width W is relatively narrow, preferably subtending an angle to the central longitudinal axis 16 of less than 30 degrees, and typically 5-20 degrees. The width must be sufficient to allow the suture (of whatever thickness is to be used) to pass through. A width of 1-2 millimeters is typically sufficient, and in many cases, the distal slot portion may be a sub-millimeter width slot.

A first transition region of slot 20 starts at a first distance $L_1$ from distal tip 18, at which first edge 26 is shaped at point "d" so as to diverge from second edge 28, while second edge 28 itself extends in an axial direction a further distance Δ to point "c". The term "axial direction" is used herein in the description and claims to refer to a direction giving the visual appearance of being parallel to central axis 16, which allows for imperfect alignment (e.g., up to about ±20 degrees off axis) and does not require that the second edge 28 is exactly straight. A second transition region starts at point "c", a second distance $L_2$ (equal to $L_1+\Delta$) from the distal tip, at which second edge 28 diverges from the axial direction away from first edge 26.

Figure 3B:
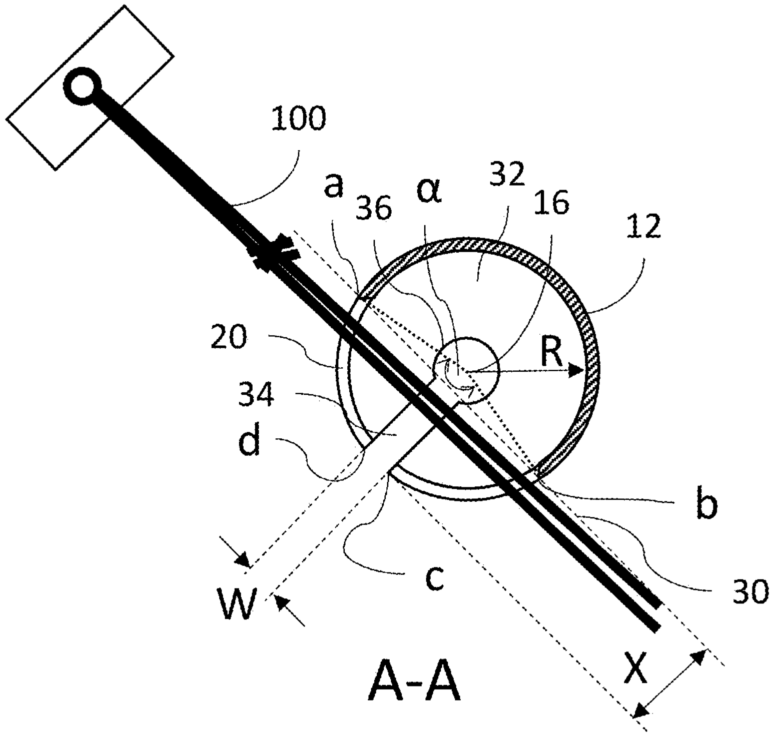
FIG. 3B is a schematic cross-sectional view taken along the line A-A of FIG. 3A.
Figure 3C:
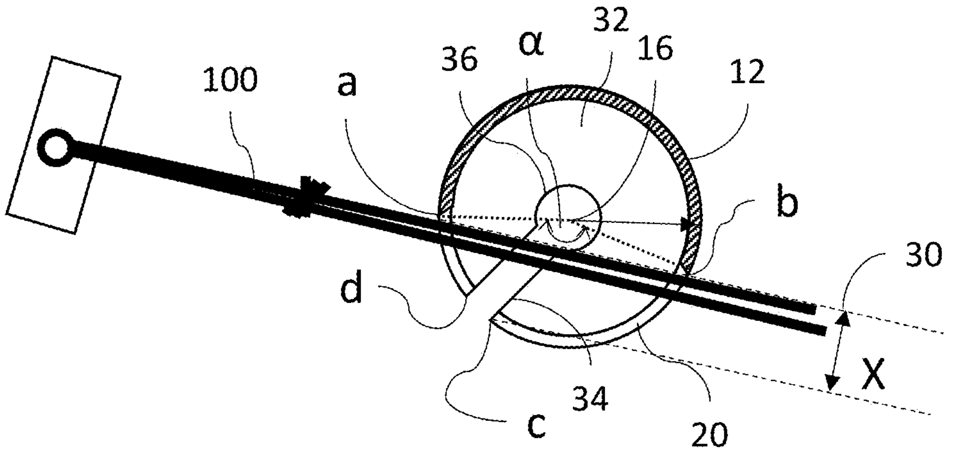
FIG. 3C is a view similar to FIG. 3B illustrating a variant geometry of the suture-receiving slot of FIG. 3A.

The first edge 26 in the first transition region and the second edge 28 in the second transition region define at least part of an oblique groove crossing the tubular wall for receiving a suture. The significance of this structure may be understood with reference to FIGS. 3B and 3C, where the oblique groove is visible as the part of the cylindrical wall which is seen to be open in the cross-sectional view. This allows the suture to be inserted across the groove to a "maximum depth" corresponding to a base line 30 of the groove, from region "a" of edge 26 to region "b" of edge 28. As seen in FIGS. 3B and 3C, point "c", corresponding to a region of second edge 28 at a beginning of the second transition region, provides a suture-capturing prominence (locally-projecting region), which is at a height X from base line 30 (or more precisely, a base plane passing through base line 30 and parallel to the central axis 16). This height X is preferably larger than first width W of the distal slot portion, and is preferably at least 30% of a radius R of the tubular wall of the tubular suture holder. This height, together with the staggered shape of the slot, with point "d" closer to the distal tip than point "c", provides a highly effective geometry for catching the suture for insertion into the device.

Figure 4A:
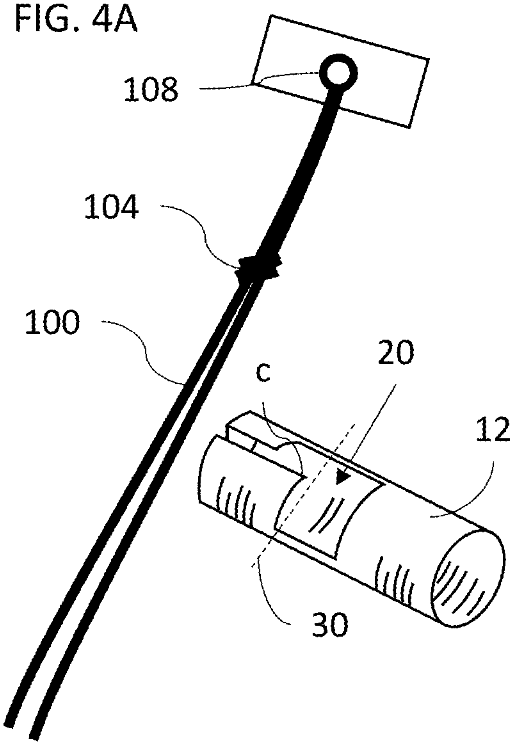
FIGS. 4A-4D are schematic illustrations of successive stages in a process of loading a suture into the knot pusher of FIG. 1A.
Figure 4B:
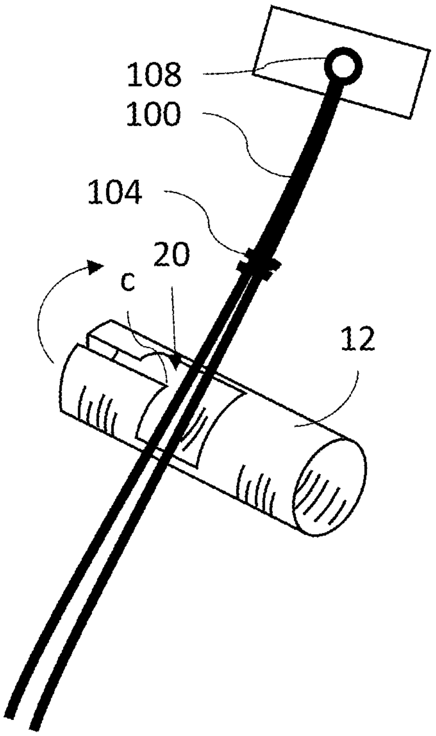
Figure 4C:
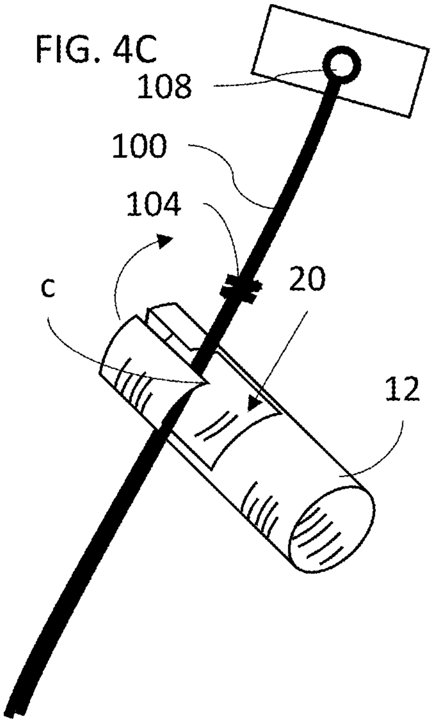
Figure 4D:
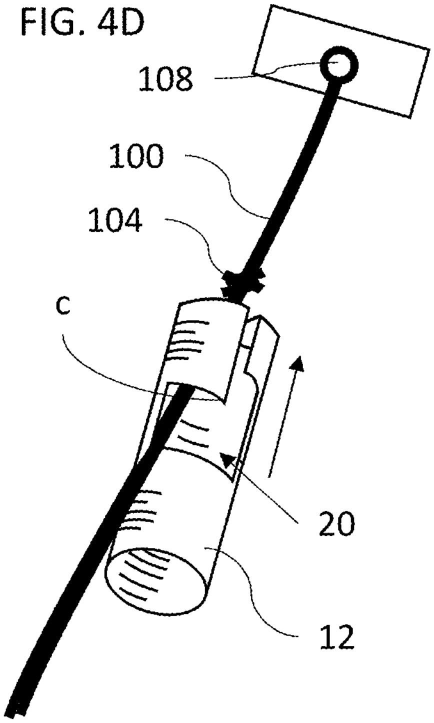

The typical sequence for catching a suture and inserting it along the slot is illustrated in FIGS. 4A-4D. The knot pusher is brought close to the suture(s) to be engaged (FIG. 4A) and is positioned so that the suture lies across the base of the groove (FIG. 4B). In this position, suture-capturing prominence "c" is raised above the suture, thereby facilitating catching the suture, typically through a rotating motion of the knot pusher, as illustrated in FIG. 4C. Once the suture is caught under prominence "c", further rotation of the knot pusher causes the suture to slide along edge 28 and to be guided through the narrow distal slot portion to the position of FIG. 4D, ready for closure of the gate by displacement of the mandrel (not shown here). Although presented here as a sequence of steps/positions, the entire sequence is typically formed intuitively in a swift single motion. Unlike various conventional knot pushers, this suture capturing motion can be performed without requiring rotation of the device around its longitudinal axis, thereby making the manipulation easy and intuitive.

The depth of the groove is preferably a relatively large part of the thickness of the tubular wall, while at the same time leaving a sufficient part of the tubular wall to provide structural integrity. Typically, the oblique groove corresponds to an opening through the tubular wall which subtends a groove angle α of between 120 degrees and 240 degrees about the central longitudinal axis, measured from the angular extremities of first edge 26 and second edge 28, which may occur at the same axial position along the groove or may be staggered. Even if these angular extremities occur at the same axial position along the groove, the groove is still referred to as an "oblique" groove, due to the asymmetry between edges 26 and 28, with edge 26 broadening outwards more distally than edge 28. It is a particular feature of certain particularly preferred implementations of the present invention that an angular position of the distal slot portion (defined, for example, as a direction of a midpoint on a chord between "c" and "d" relative to the central longitudinal axis) is angularly spaced away from the ends of the oblique groove by at least about 20 degrees. In the example of FIG. 3B, the distal slot portion is roughly central to the groove angle, whereas in FIG. 3C, the distal slot portion is asymmetrically located relative to the groove angle. So long as the distal slot portion is significantly spaced away from the extremities of the groove angle, such as by at least about 20 degrees, suture-capturing prominence "c" will be sufficiently raised above the resting position to the suture within the groove to facilitate reliably catching the suture. The height of point "d" above the groove base line also defines an obstacle which is readily overcome during insertion of the suture, such as by the rotation motion described above with reference to FIGS. 4C and 4D, but helps to reduce the likelihood of the suture unintentionally escaping from the distal slot portion during use, since the slot is essentially upward facing, and not in the direction in which tension is typically applied to the suture ends.

Figure 10A:
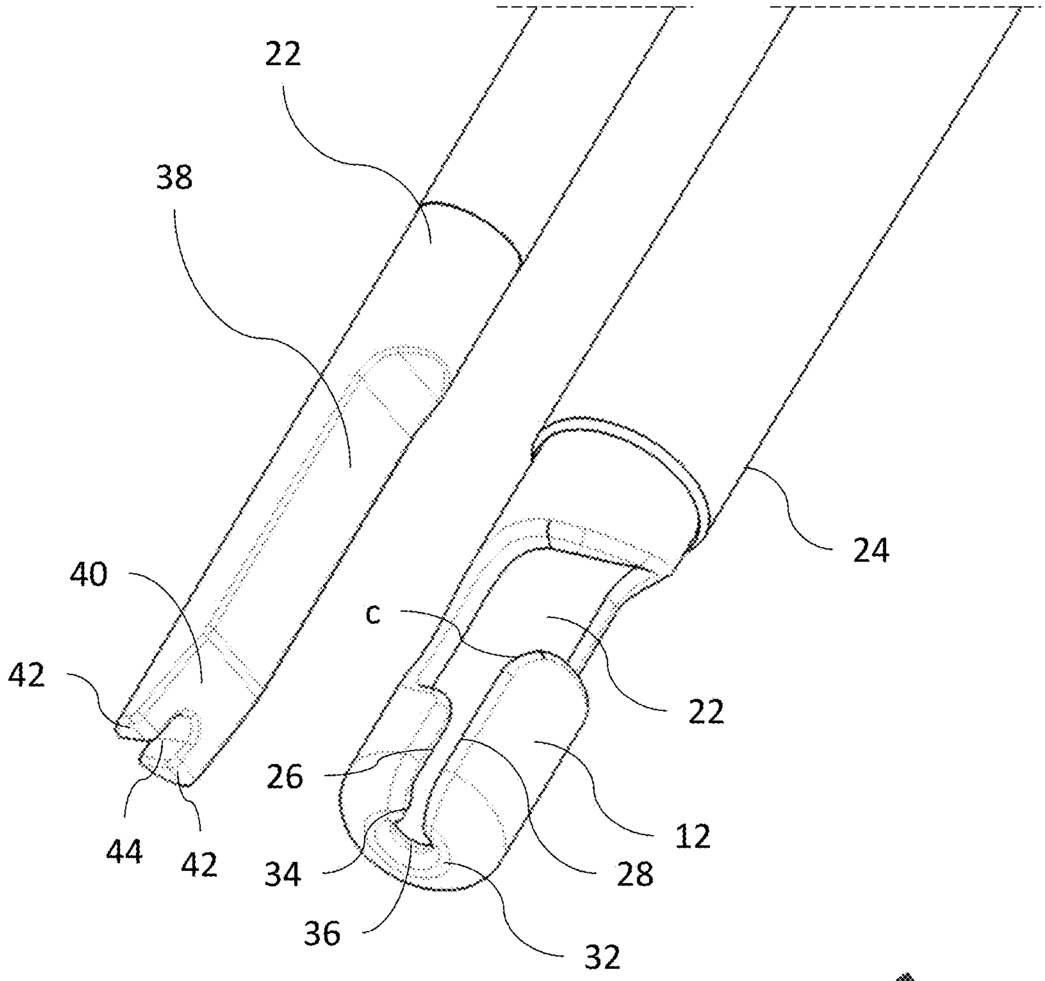
FIG. 10A is an isometric view of the distal portions of the tubular suture holder and the mandrel when separated.
Figure 10B:
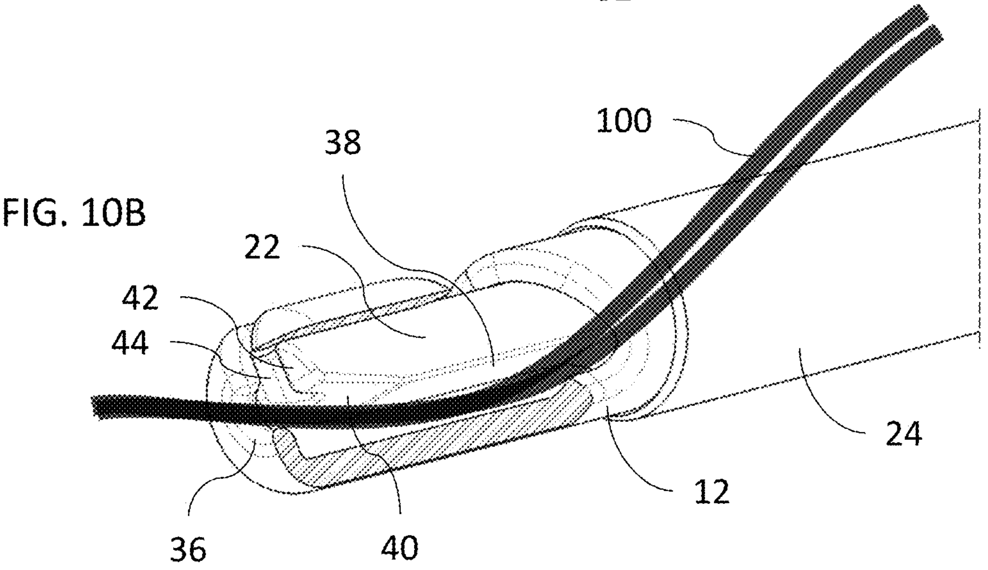
FIG. 10B is a partially cut-away isometric view of the assembled knot pusher illustrating the path of a loaded suture thread through the tubular suture holder.

To facilitate pushing knots so that they do not enter the internal bore of the tubular suture holder, as seen in FIGS. 3B, 3C and 10A, the distal tip of the tubular suture holder is preferably formed with an end closure 32 closing a majority of an area of the internal bore. End closure 32 includes a radial slot 34 that is contiguous with the distal slot portion of suture-receiving slot 20, and typically of similar width W to the distal slot portion. Radial slot 34 preferably terminates at a retaining aperture 36 having a lateral dimension that is greater than the first width W. Thus, for example, the distal slot portion and the radial slot may have a first width W sized to allow a single suture to path through the slot, while retaining aperture 36 is preferably sufficiently large to receive the total number of suture ends being used, such as when the suture ends are loaded for cutting. If a doubled-over suture thread is being used, this may require introducing four thicknesses of suture thread at once, while still being sufficiently close-fitting to prevent the sliding knot from entering the internal bore. Radial slot 34 and retaining aperture 36 typically together form a keyhole slot shape.

Figure 11A:
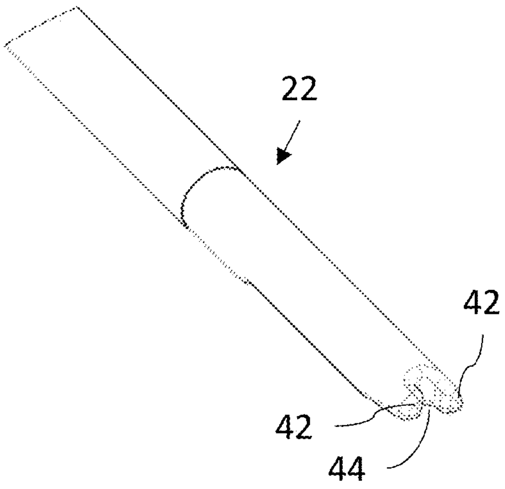
FIGS. 11A-11C are isometric views of a distal part of a mandrel from the knot pusher of FIG. 1A illustrating variant forms of a tip of the mandrel with two projecting fingers, one projecting finger, and with a flat end, respectively.
Figure 12A:
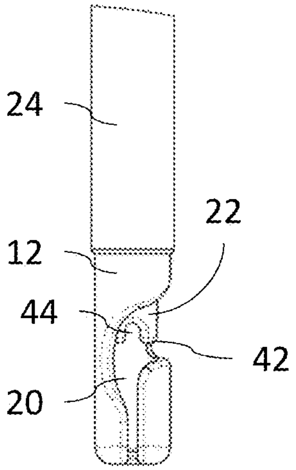
FIGS. 12A-12C are top views of the distal part of a knot pusher employing each of the implementations of the mandrel of FIGS. 11A-11C, respectively.

Turning now to features of certain preferred implementations of mandrel 22, one particularly-preferred but non-limiting example is illustrated in FIGS. 10A and 11A. At least the portion of mandrel 22 which reaches the region of suture-receiving slot 20 is formed with an indentation, channel or cut-out 38 which, together with the tubular wall of tubular suture holder 12, defines a conduit between distal tip 18 and a proximal part of the oblique groove through which the suture can slide, as best seen in the cut-away view of FIG. 10B. The cut-out 38 (so-called to describe its shape, without limiting the device to any particular production technique) may be a flat surface which corresponds to a cut-out of less than half of a cylindrical shape. In that case, a distal chamfer surface 40 may advantageously provide additional clearance to allow free running of the suture via retaining aperture 36.

According to a further aspect of the present invention, according to certain particularly preferred embodiments, mandrel 22 terminates in at least one projecting finger 42, having a cross-sectional area that is less than half of a cross-sectional area of mandrel 22 proximal to projecting finger 42. In the example of FIGS. 10A and 11A, mandrel 22 has two projecting fingers 42, such that it can alternatively be viewed as a bifurcated tip, or as a tip with a recess or "notch" 44. Notch 44 is preferably aligned with the distal slot portion, so that tension applied to a suture acting to pull it in a reverse direction through the distal slot portion will tend to engage the suture with notch 44. Notch 44 is preferably sized to receive simultaneously all of the suture thread thicknesses that may be loaded into the knot pusher during tightening of knots.

Figure 13A:
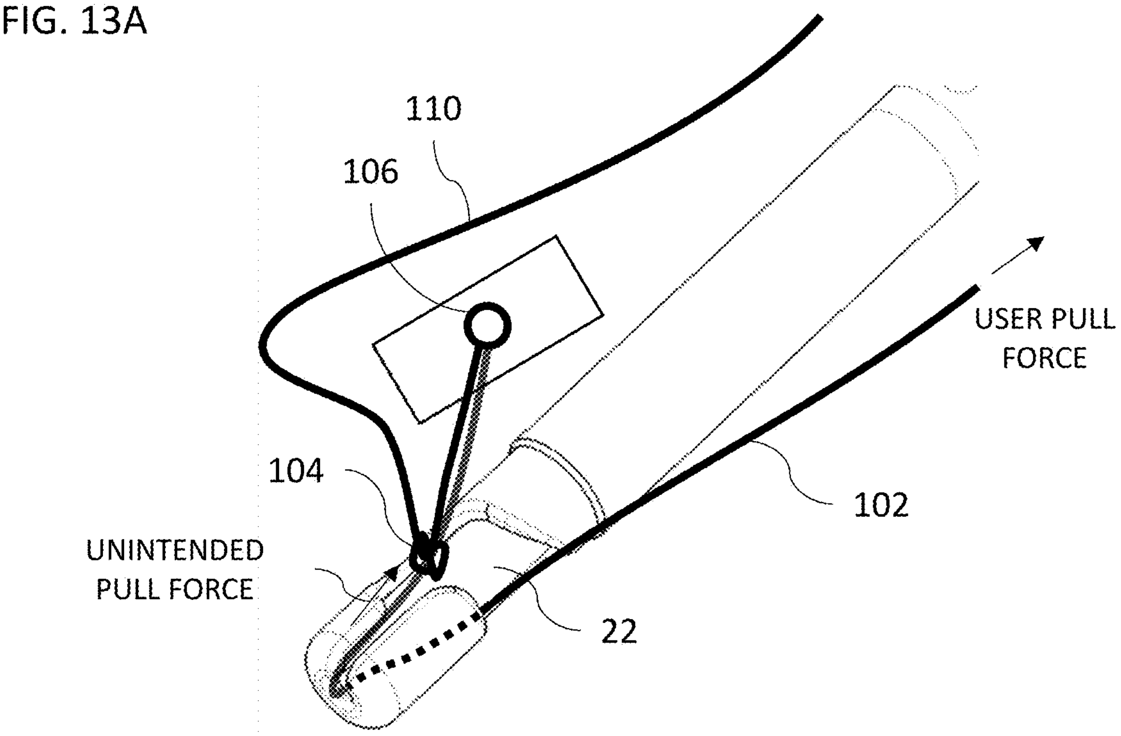
FIGS. 13A and 13B are schematic isometric views of the distal part of the knot pusher of FIG. 12A under conditions of excess unintended retraction forces, with the suture gate closed and partially open due to the retraction forces, respectively.
Figure 13B:
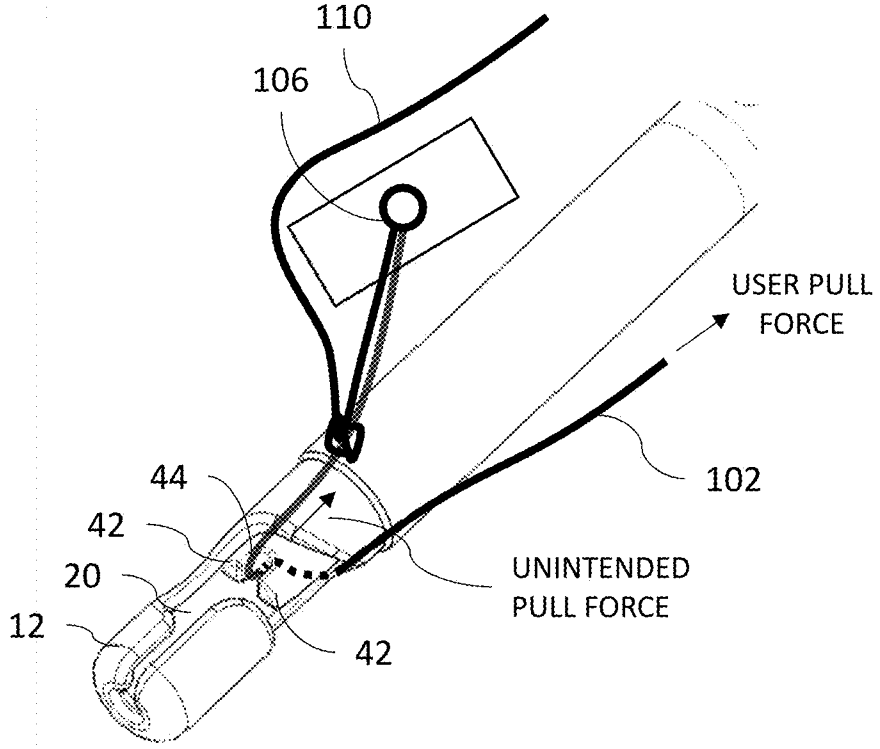

The resulting functionality is illustrated in FIGS. 13A and 13B. In various situations, particularly if the tip of the knot pusher is inserted deeper into the target tissue than the tissues being sutured, tension applied by the user on the rail thread and the locking thread may result in significant proximal force applied directly to the suture gate. Due to the positioning of the distal slot portion towards to "top" of the knot pusher tip, in most cases, these forces act on the sides of the retaining aperture 36. However, in some cases, if the suture becomes aligned with the distal slot portion, these proximal forces may tend to force retraction of the mandrel 22 and could potentially allow escape of the suture. Projecting finger(s) 42 and notch 44 help to prevent escape of the suture.

Specifically, when a suture 100 is trapped by mandrel 22 in suture-receiving slot 20, as described previously, tension in the suture tending to retract the mandrel towards the retracted position engages the suture with the projecting finger(s) 42 (e.g., in notch 44) so as to inhibit release of the suture. Thus, increasing force may cause retraction of mandrel 22 as illustrated in FIG. 13B, but the tension maintains engagement of suture 100 with notch 44 so that the suture does not slip out of the suture gate. When the situation (such as over-insertion etc.) that caused the excess retraction force is remedied, the spring bias acting to advance mandrel 22 is effective to restore the normally-closed state of the suture gate.

Figure 14A:
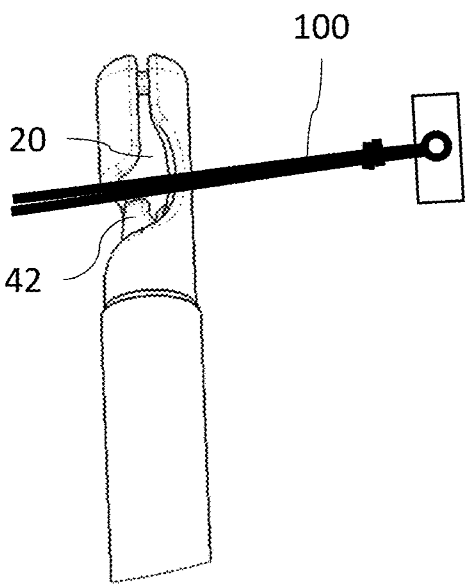
FIGS. 14A-14C are schematic top views of the distal part of the knot pusher of FIG. 12A illustrating stages during loading of a suture into the knot pusher assisted by distal displacement of the mandrel.
Figure 14B:
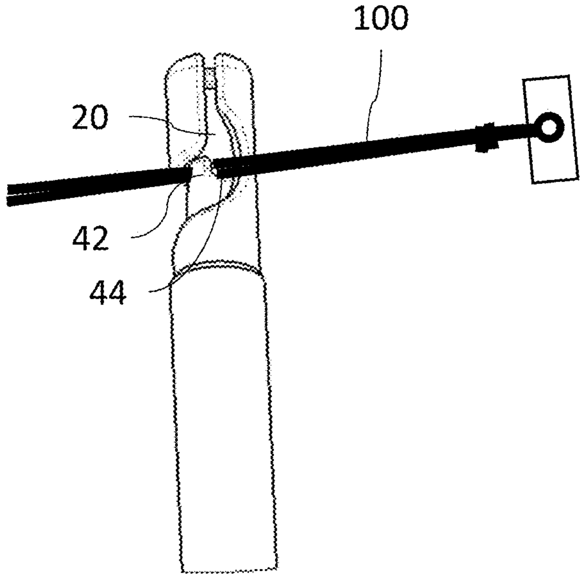
Figure 14C:
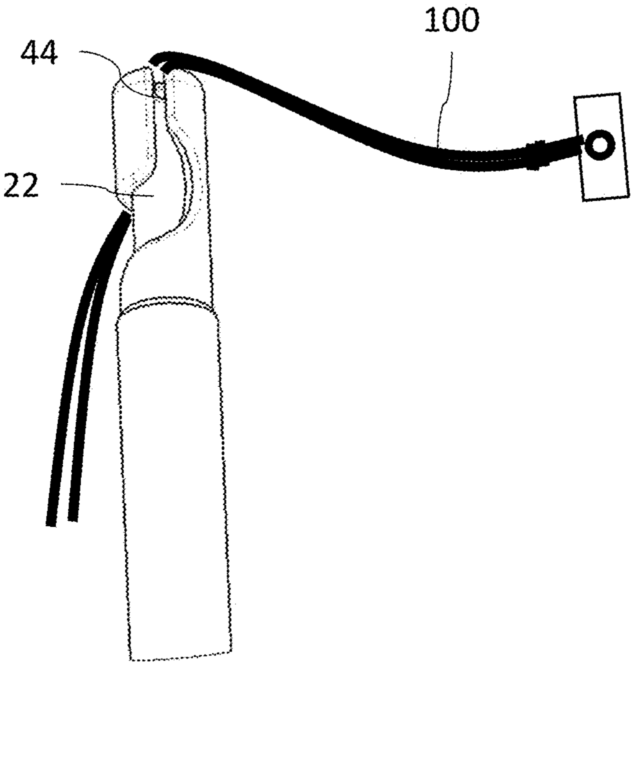
Figure 16A:
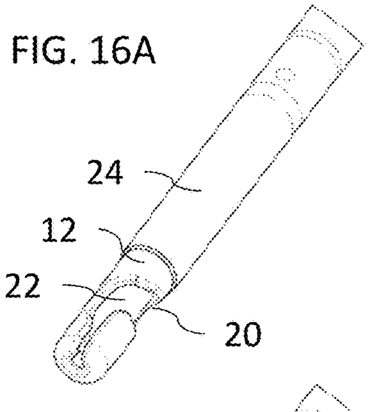
FIGS. 16A-16D are isometric views of a distal portion of the knot pusher of FIG. 1A showing the configuration of the knot pusher corresponding to each of the states of FIGS. 15A-15D.
Figure 15A:
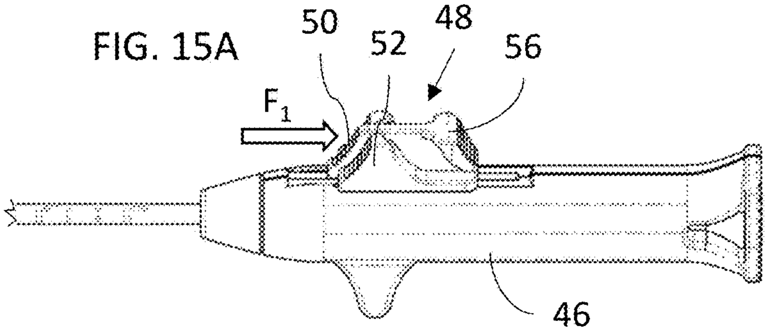
FIGS. 15A-15D are isometric views of a handle of the knot pusher of FIG. 1A illustrating the configuration of a slider arrangement in a locked state, an unlocked state, a mandrel-retraction state and a suture-cutting state, respectively.
Figure 16B:
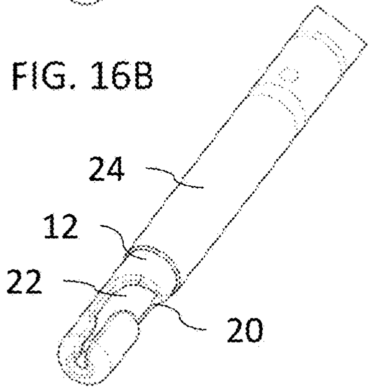
Figure 15B:
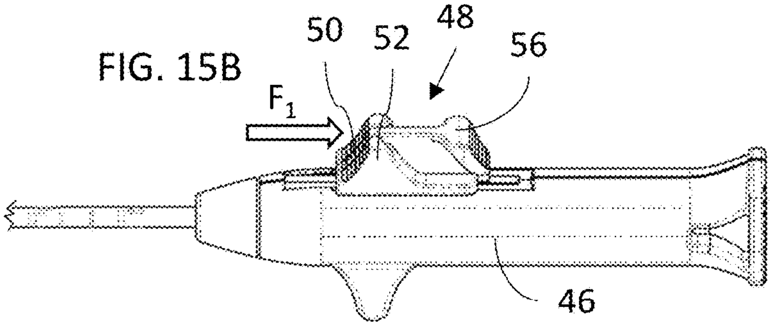
Figure 16C:
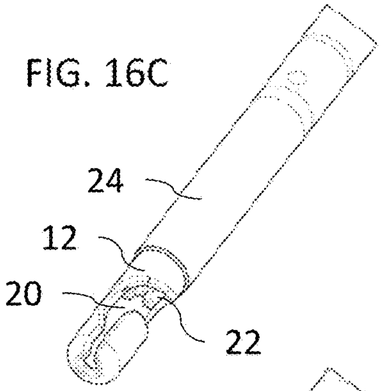
Figure 15C:
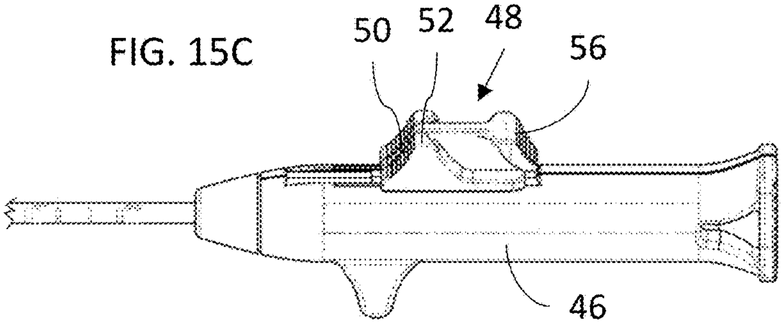
Figure 16D:
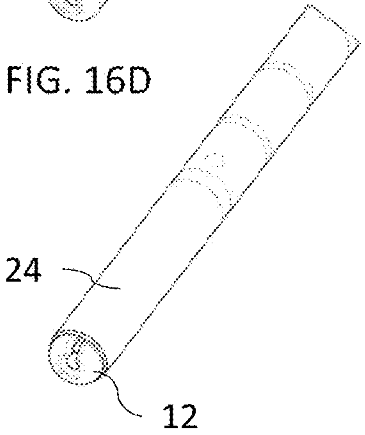
Figure 15D:
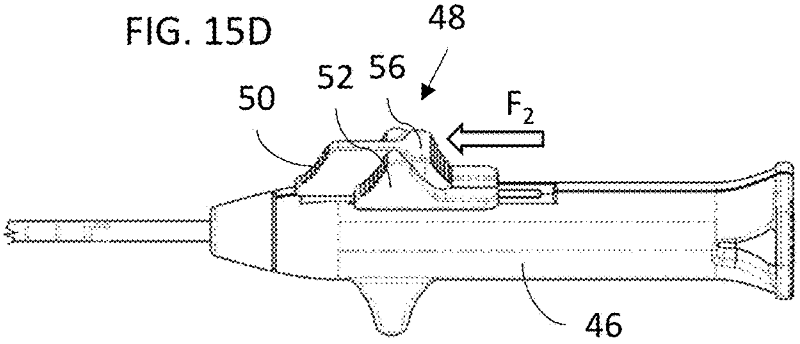
Figure 17:
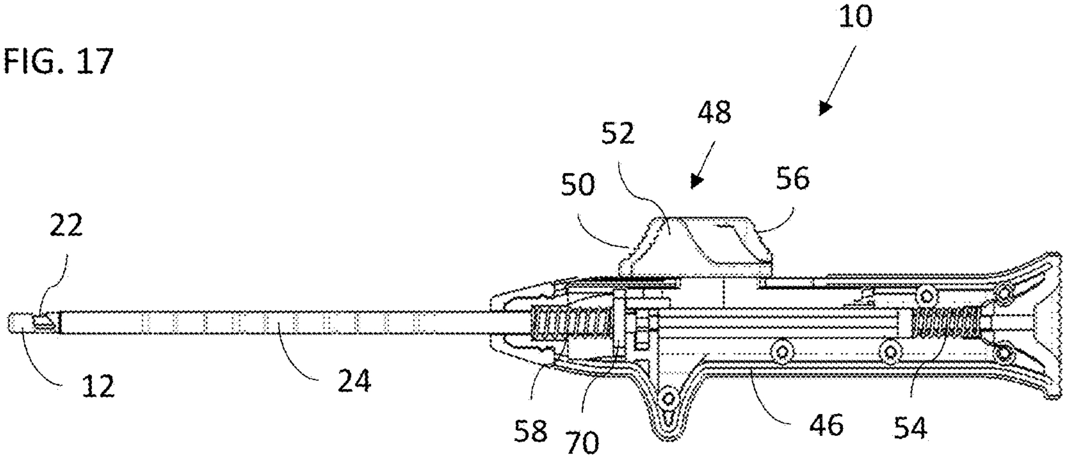
FIG. 17 is a side view of the knot pusher of FIG. 1A with a half-shell of a handle body removed to reveal the internal components.
Figure 18:
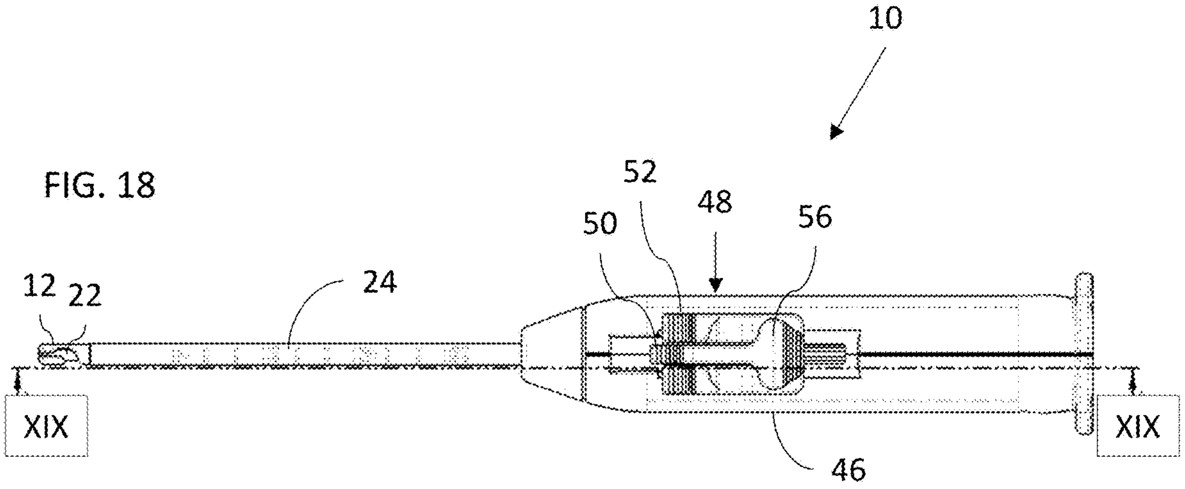
FIG. 18 is a plan view of the knot pusher of FIG. 1A.

FIGS. 14A-14C illustrate an additional possible function of the aforementioned preferred features mandrel 22. Although the process of insertion of suture 100 into the suture-receiving slot 20 was described above (FIGS. 4A-4D) as being performed by manipulation of tubular suture holder 12 while mandrel 22 is retracted and the suture gate is open, certain preferred implementations of mandrel 22 as described herein facilitate loading of the suture into the knot pusher. Specifically, as before, suture 100 is positioned across the oblique groove as illustrated in FIG. 14A while mandrel 22 is retracted. As mandrel 22 is released to return towards its distal position, one of projecting fingers 42 engages suture 100 (FIG. 14B) and carries it distally so as to pass along the suture-receiving slot 20 to its engaged position with the suture gate closed, as illustrated in FIG. 14C.

Figure 11B:
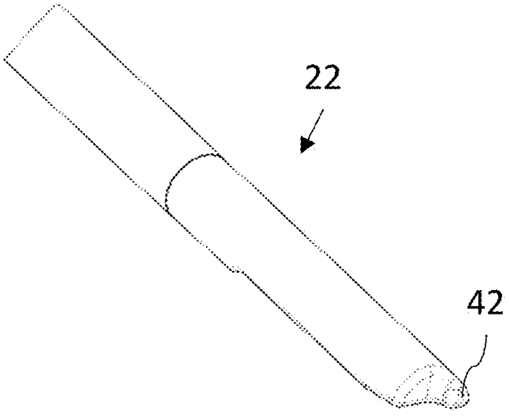
Figure 12B:
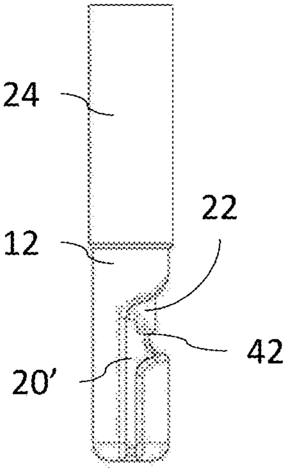
Figure 11C:
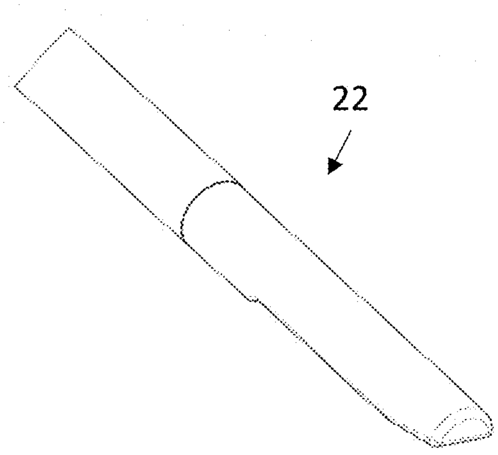
Figure 12C:
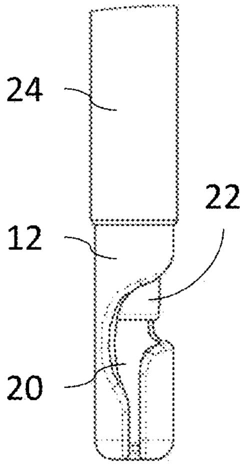

The two-finger configuration of FIG. 11A is particularly suited to the form of slot 20 described above, providing support against the suture threads slipping off in either direction into the oblique groove. An alternative configuration with a single projecting finger 42 is illustrated in FIG. 11B. This configuration may be optimal for knot pushers with a straight-edged slot 20' as illustrated in FIG. 12B, where the edge of the slot prevents escape of suture threads to one side, and a single projecting finger 42 is sufficient to retain the suture threads against slipping off towards the open proximal region of the slot. In this case, mandrel 22 can be viewed as having a stepped end. This configuration also provides the functionality described with reference to FIGS. 13A-13B and 14A-14C.

The features of mandrel 22 described here may be used to advantage together with the features of suture-receiving slot 20 described above, but are not limited to use in such a combination. Thus, for example, the suture-receiving slot 20 may also be used to advantage with a mandrel that does not have projecting fingers, such as the mandrel 22 illustrated in FIGS. 11C and 12C. Conversely, the mandrels of FIGS. 11A and 11B may be used to advantage with a knot pusher which employs a conventional suture-receiving slot, where the finger(s) 42 and/or notch 44 are deployed in the appropriate alignment to a slot at the distal-most portion of a suture gate so as to obstruct slipping-out of the suture in the event of excess tension being applied to the suture in alignment with the gate.

Figure 2C:
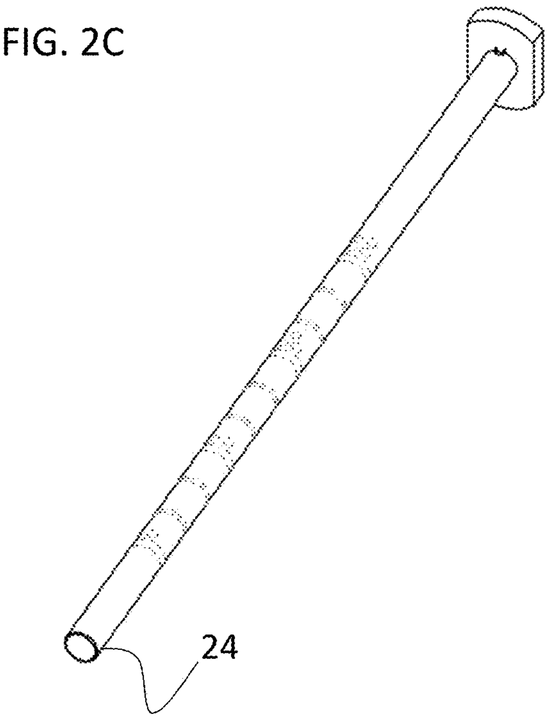

Although the features of knot pusher 10 described thus far can be implemented in a knot pusher without suture-cutting features, it is considered particularly advantageous to combine the knot-pusher functionality with suture-cutting capability. For this purpose, certain preferred embodiments of the present invention include a cutting element 24, typically implemented as a cylindrical tube terminating at a sharp cutting edge (FIG. 2C). In the embodiments described thus far, the cutting element circumscribes tubular suture holder 12 externally. Cutting element 24 is biased to a withdrawn (proximal) position, and is selectively displaceable in a distal direction as shown in FIG. 9B to cut a suture exiting via a proximal portion of suture-receiving slot 20. Where cutting element 24 is the outermost element of the shaft of the device, it is preferably provided with a series of depth indications (visible for example in FIG. 2C) to facilitate insertion of the knot pusher to the correct depth during a minimally-invasive procedure. In an alternative implementation illustrated in FIGS. 22A-22C, cutting element 24 is deployed internally to tubular suture holder 12. The functionality is essentially unchanged.

A further aspect of the present invention relates to a knot pusher and suture cutter which provides an advantageous user interface for operating the knot pusher and suture cutter, with a self-locking and easy-to-release functionality. This aspect of the invention will be described, by way of one non-limiting example, in the context of a knot pusher and suture cutter that incorporates the other aspects of the present invention described above. However, this aspect of the present invention may also be used to advantage with a knot pusher and suture cutter having a tubular suture holder that may have a different form of suture-receiving slot from that described above, and different forms of displaceable mandrel for opening and closing the suture gate, as well as an axially-displaceable cutting element, external or internal to the tubular suture holder.

In general terms, a knot pusher and suture cutter according to this aspect of the present invention includes a handle 46 supporting tubular suture holder 12, and a manually operable slider arrangement 48 for controlling operation of both the mandrel and the cutting element.

Manually operable slider arrangement 48 is configured such that an axial force $F_1$ (FIGS. 15A-15B) applied to the slider arrangement 48 in a first axial direction acts against a spring arrangement to displace mandrel 22 from its advanced (closed) position to its retracted (open) position, and an axial force $F_2$ applied to the slider arrangement 48 in a second axial direction opposite to the first axial direction acts against the spring arrangement to displace the cutting element 24 to cut a suture exiting via a proximal portion of the suture-receiving slot 20 (as explained above with reference to FIG. 9B).

It is a particularly preferred feature of certain implementations of this aspect of the present invention that slider arrangement 48 includes a locking configuration which locks the mandrel against displacement in the retraction direction, thereby preventing retraction of the mandrel due to tension applied to the suture ends, and that the locking configuration is released by an initial motion caused by manual displacement of a release element 50 in the first axial direction at the beginning of the mandrel opening motion, before the mandrel itself moves.

The internal components of a slider arrangement and spring arrangement according to one particularly-preferred but non-limiting exemplary implementation are revealed in FIGS. 17-20C. In this case, slider arrangement 48 includes a first slider 52, mechanically linked to mandrel 22, and biased to a forward (distal) position by a mandrel spring 54, and a second slider 56, deployable to displace cutting element 24, which is biased to a retracted position by a cutting-element spring 58.

Figure 19A:
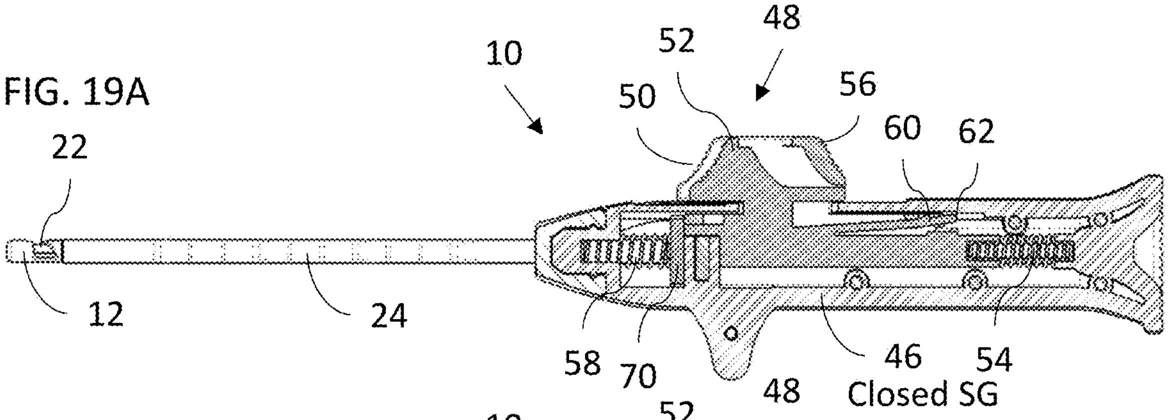
FIGS. 19A-19D are cross-sectional views taken along the line XIX-XIX in FIG. 18 corresponding to the states of FIGS. 15A-15D, respectively.
Figure 19B:
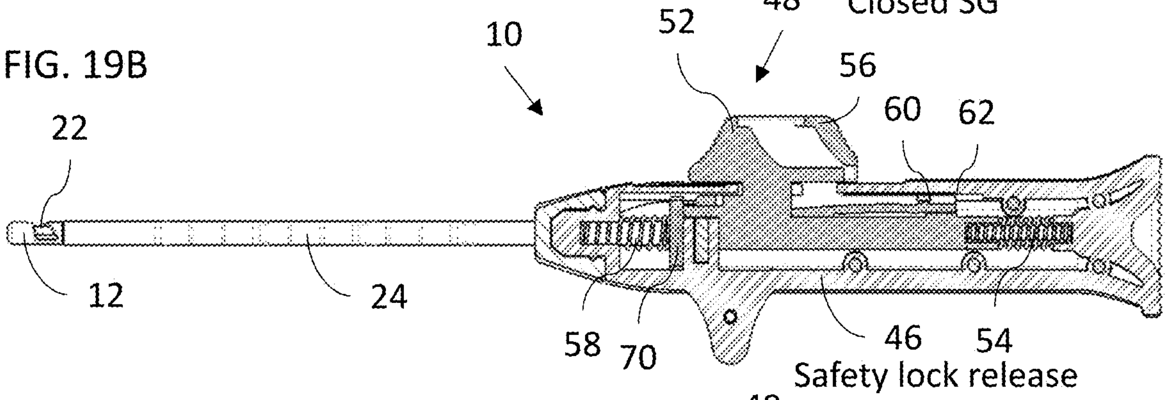
Figure 19C:
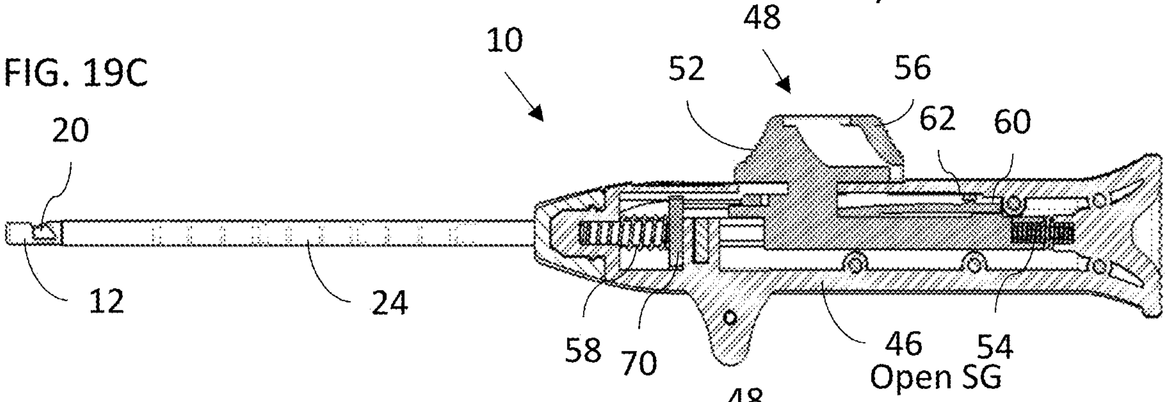
Figure 19D:
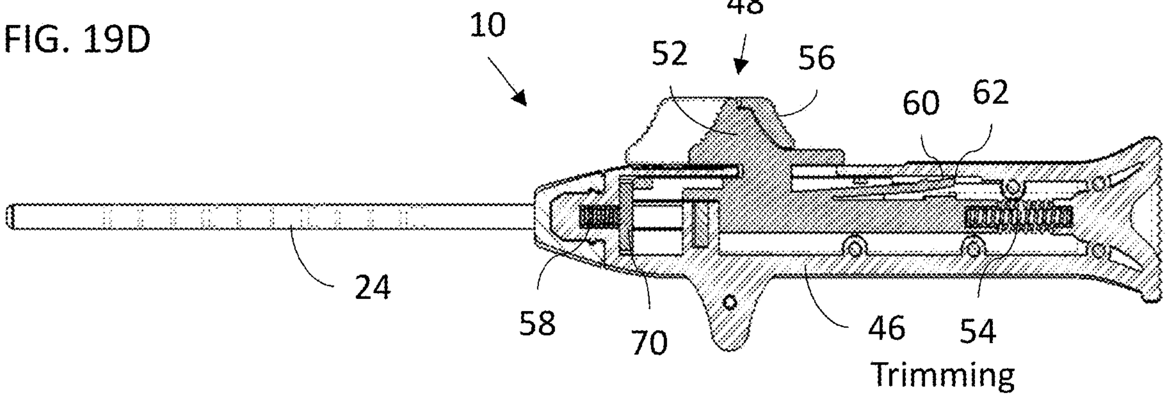

Locking of mandrel 22 against unintended retraction is provided by a locking configuration, here implemented as one or more resilient blocking elements 60 associated with first slider 52 and deployed so as to abut a shoulder 62 formed in the body of handle 46, as best seen in FIG. 19A. In this implementation, second slider 56 provides a projecting surface which, in the resting state of the mechanism, projects slightly in a distal direction from the contact surface of first slider 52 to provide the manually-displaceable release element 50. When manual pressure is applied to release element 50, typically by the user's thumb, a first stage of motion brings release element 50 in line with first slider 52 (motion from FIG. 19A to FIG. 19B) which is effective to deflect resilient blocking elements 60 sufficiently to pass shoulder 62, thereby unlocking the locking configuration. Further motion of the user's thumb is then effective to displace first slider 52 (together with second slider 56) in a proximal direction against mandrel spring 54, thereby withdrawing mandrel 22 proximally to open the suture gate, as described earlier. When the sliders are released, mandrel spring 54 returns the sliders to their initial position, thereby advancing mandrel 22 to its closed position, closing the suture gate and reengaging the locking configuration.

Figure 20A:
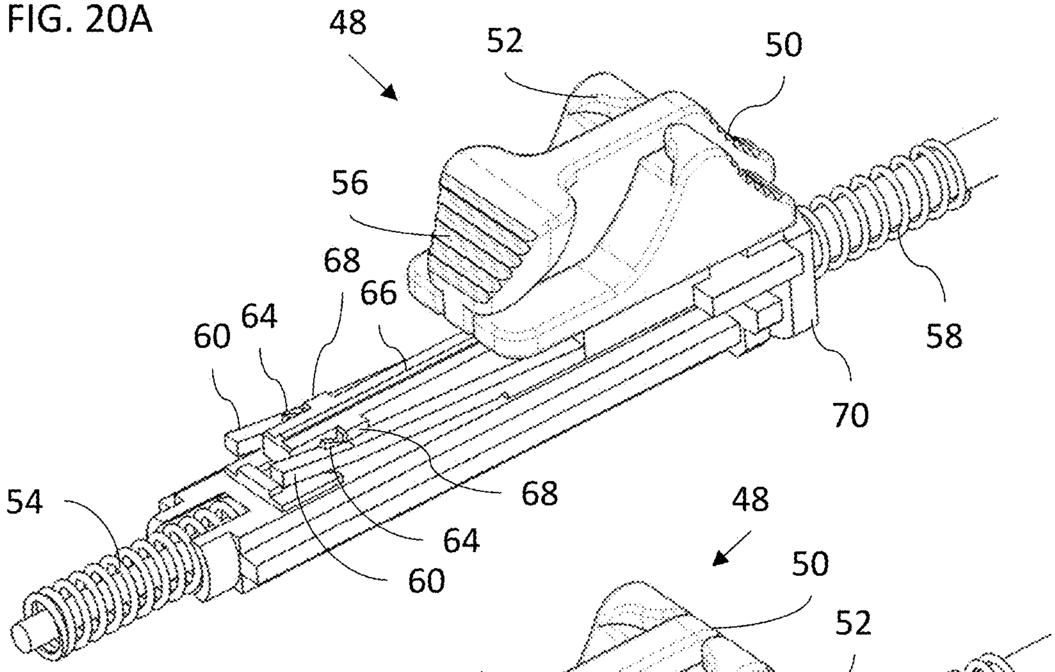
FIGS. 20A and 20B are enlarged isometric views of a slider arrangement from the knot pusher of FIG. 1A illustrating a locking configuration in a locked state and an unlocked state, respectively.
Figure 20B:
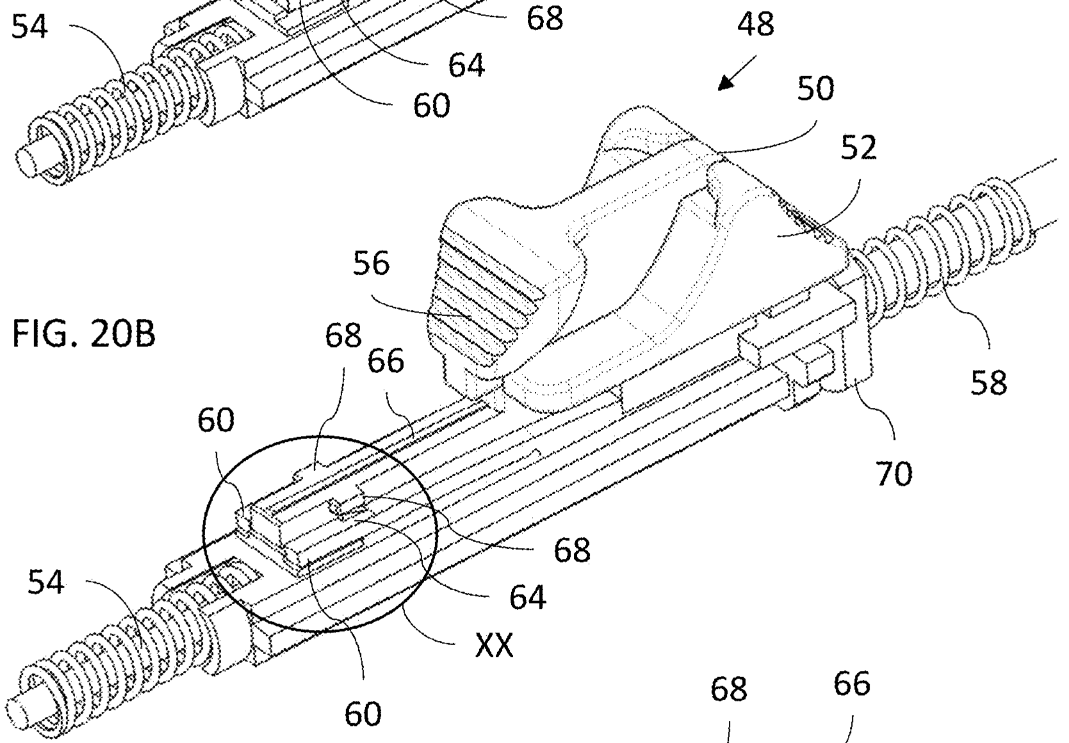
Figure 20C:
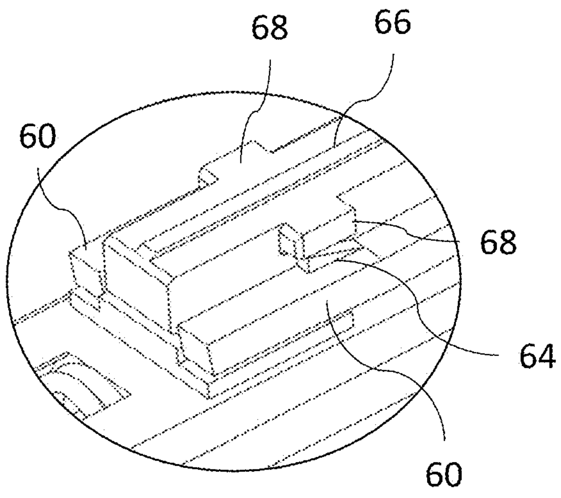
FIG. 20C is an enlarged view of the region of FIG. 20B designated XX.

More detail of one non-limiting but particularly preferred implementation of the release mechanism is shown in more detail in FIGS. 20A-20C. Resilient blocking elements 60 are shown here with integrally-formed wedge formations 64, while second slider 56 has an associated actuator rod 66 with lateral projections 68 deployed to interact with wedge formations 64. When release element 50 is displaced proximally, lateral projections 68 ride up over wedge formations 64, thereby depressing resilient blocking elements 60 sufficiently to clear the blocking shoulder 62 of the housing. After release of first slider 52 and its return to its distal position, second slider 56 is returned to its forward position by the resilient force of blocking elements 60 acting on the lateral projections 68, thereby relocking mandrel 22 against retraction.

When second slider 56 is manually pushed in a distal direction (FIG. 19D), this forces a flange 70 associated with the cutting element tube in a distal direction against cutting-element spring 58, thereby advancing the cutting element to cut the suture(s), as described above.

Figure 21:
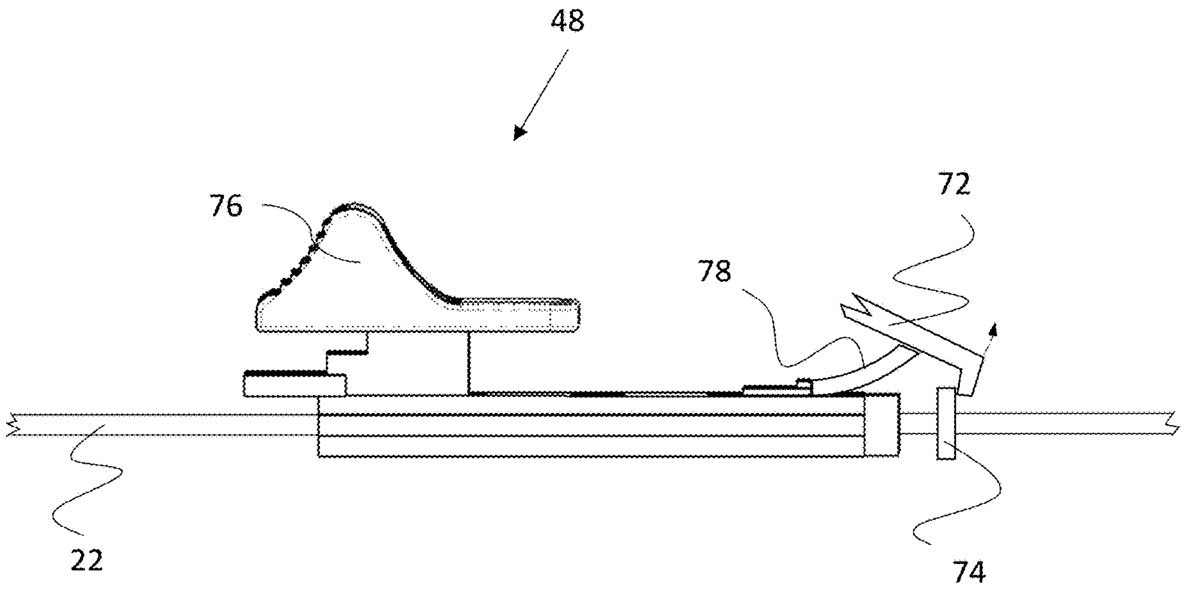
FIG. 21 is a schematic side view of an alternative slider arrangement for use in the knot pusher of FIG. 1A.
Figure 22A:
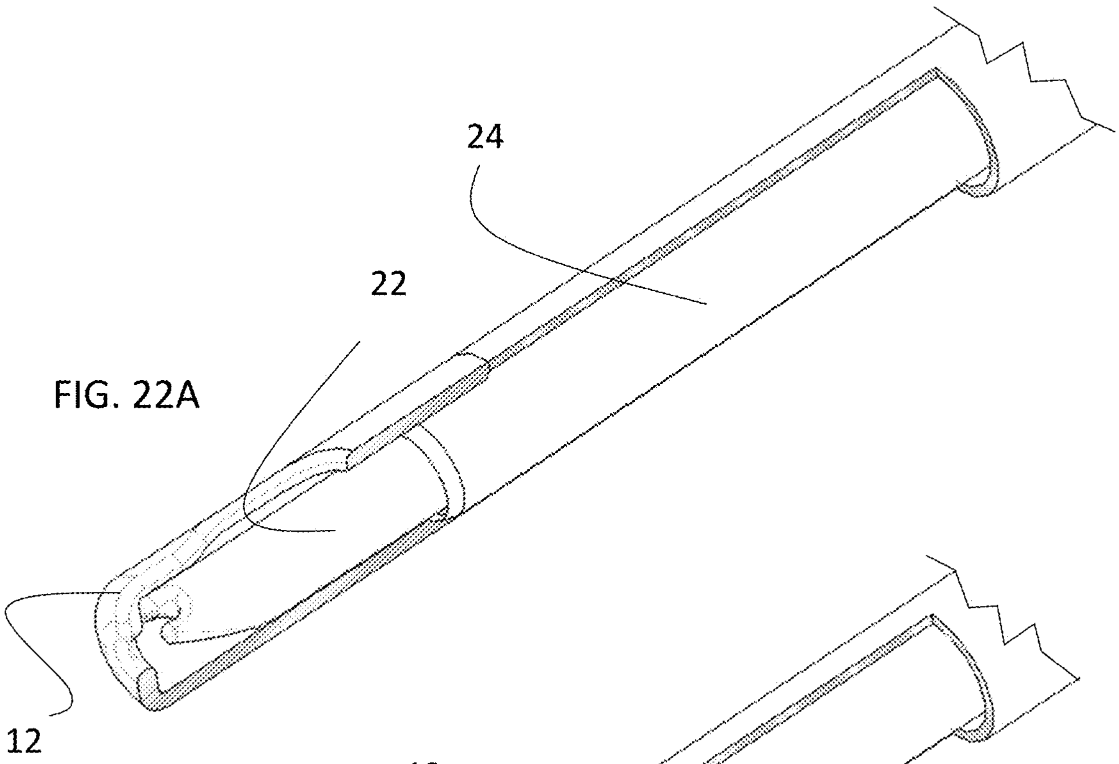
FIGS. 22A and 22B are partially cut-away isometric views of a distal portion of the knot pusher of FIG. 1A according to a variant implementation in which a cutting element is deployed internally to a tubular suture holder, shown with the cutting element in a retracted and a distally-deployed cutting position, respectively.
Figure 22B:
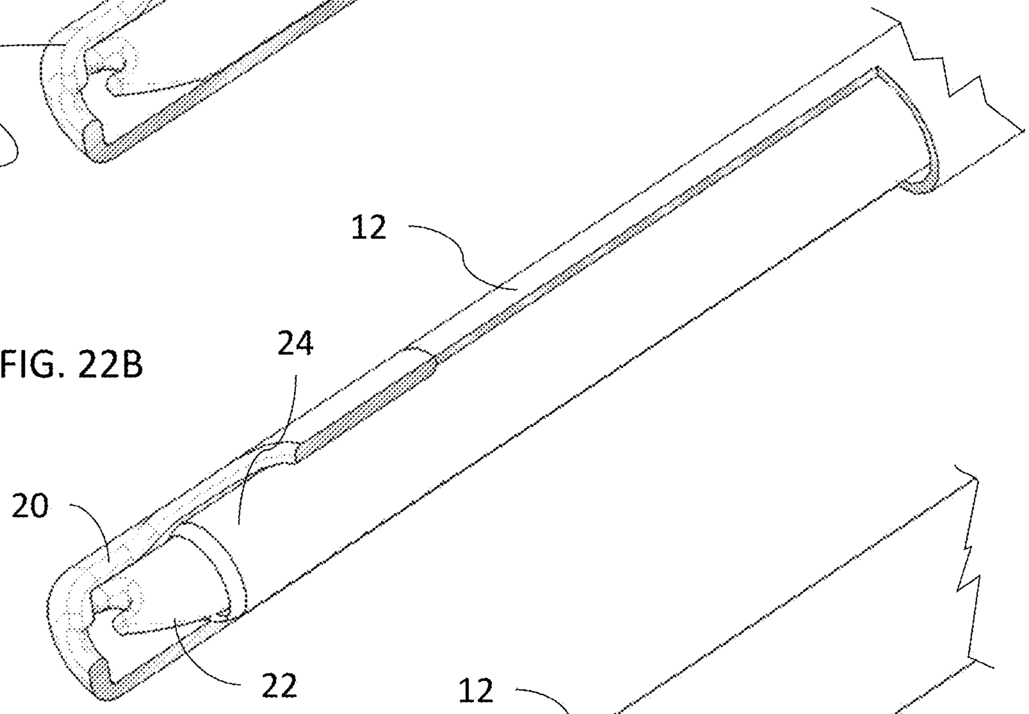
Figure 22C:
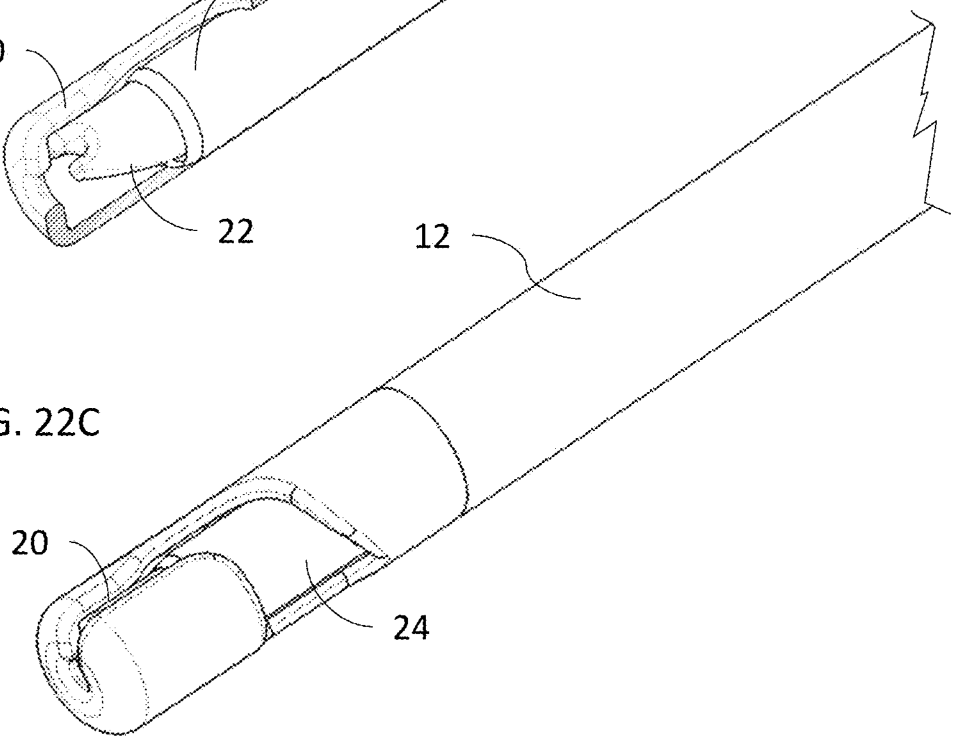
FIG. 22C is a view similar to FIG. 22B but not cut away.
Figure 23A:
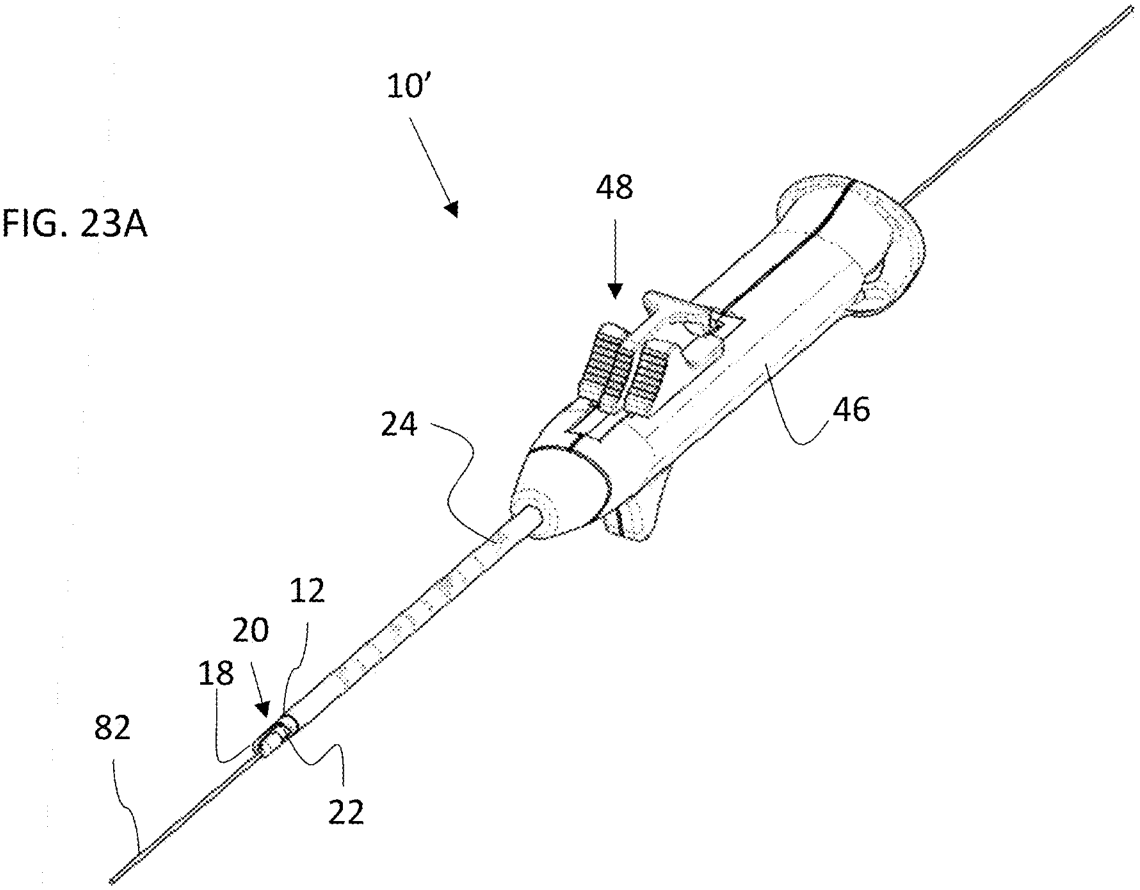
FIGS. 23A and 23B are front and rear isometric views, respectively, of a knot pusher and suture cutter, constructed and operative according to a further embodiment of the present invention, configured for use over-the-wire with a guidewire.
Figure 23B:
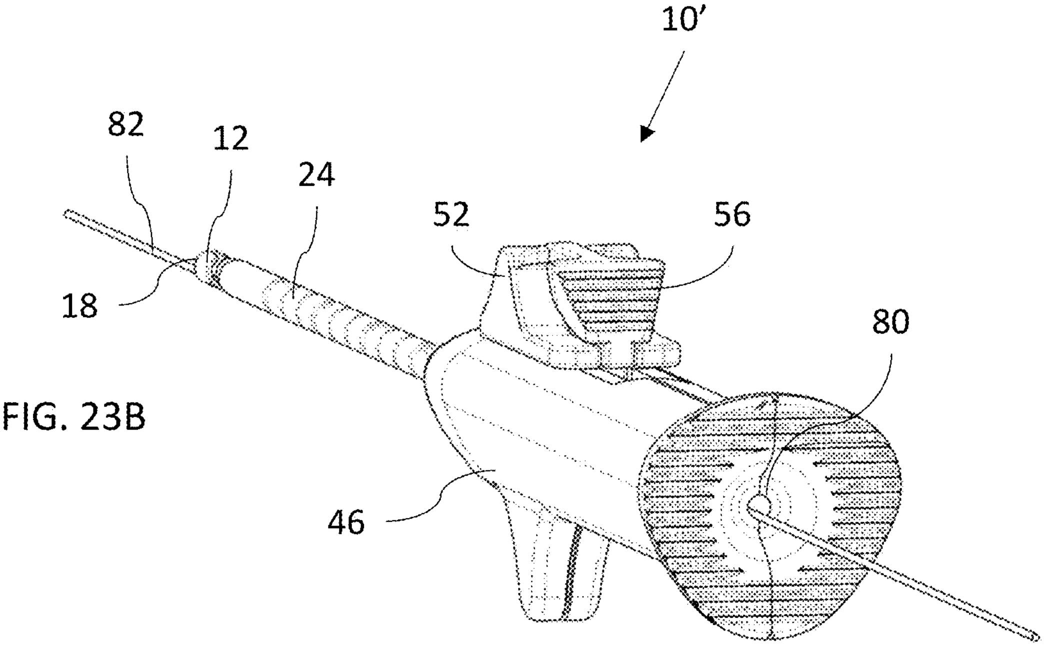
Figure 25A:
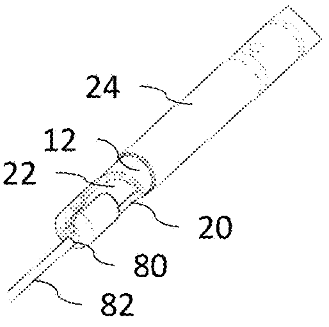
FIGS. 25A-25D are isometric views of a distal portion of the knot pusher of FIG. 23A showing the configuration of the knot pusher corresponding to each of the states of FIGS. 24A-24D.
Figure 24A:
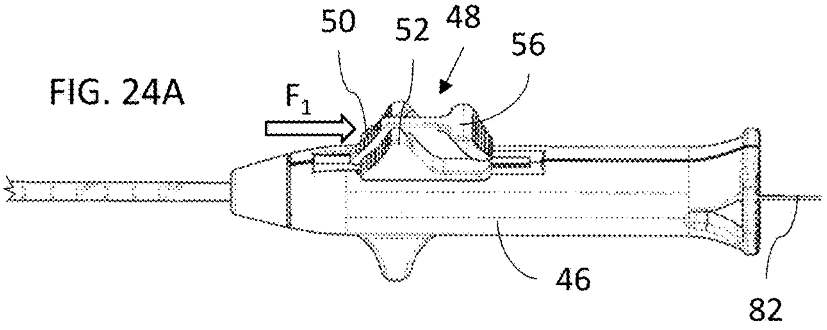
FIGS. 24A-24D are isometric views of a handle of the knot pusher of FIG. 23A illustrating the configuration of a slider arrangement in a locked state, an unlocked state, a mandrel-retraction state and a suture-cutting state, respectively.
Figure 25B:
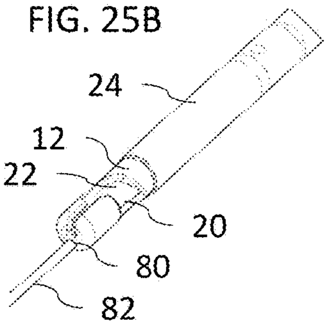
Figure 24B:
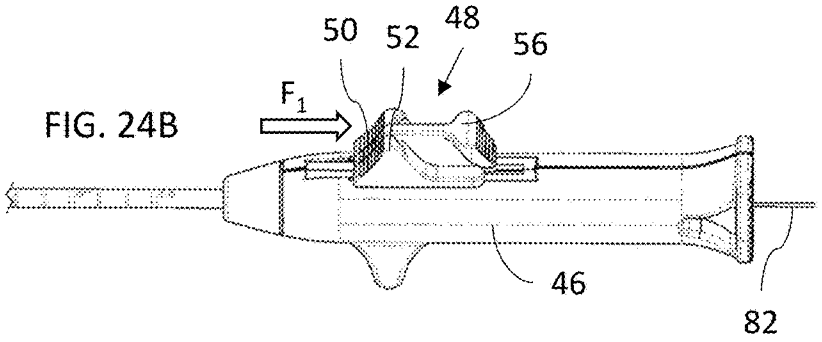
Figure 25C:
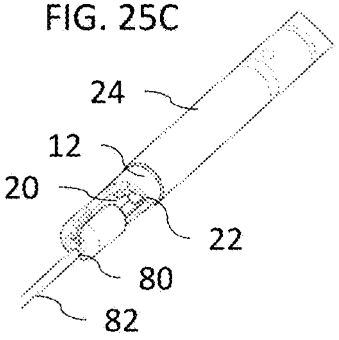
Figure 24C:
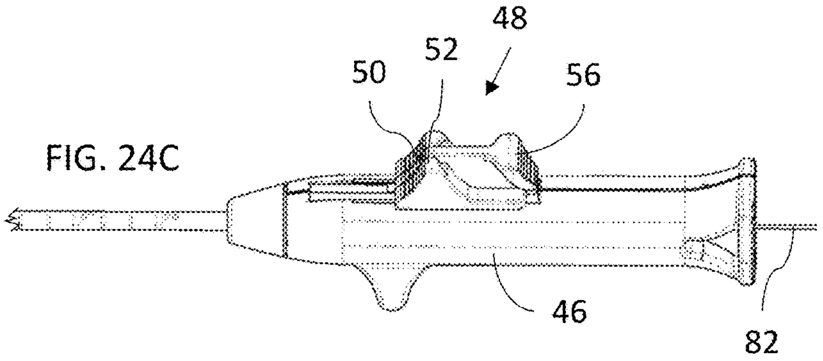
Figure 25D:
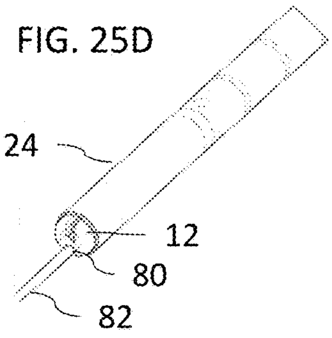
Figure 24D:
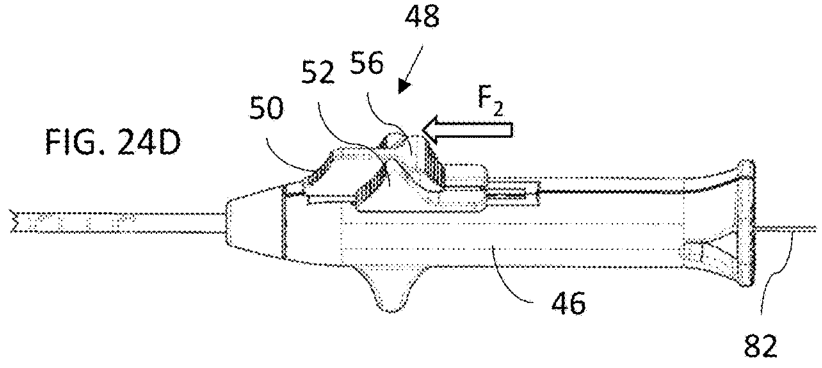

Although the slider arrangement and spring arrangement described thus far employ two discrete slider elements and two discrete springs to control the motions of the mandrel 22 and cutting element 24, the principles of operation illustrated above can also be implemented in a simpler manner using a single slider, controlled by either two springs or a single spring. A schematic illustration of a possible mandrel locking mechanism is shown in FIG. 21. Motion of mandrel 22 is blocked by a locking lever 72 which retains a mandrel flange 74 to prevent retraction. The slider 76 is positioned with a small "idle" distance spacing it from mandrel flange 74, and has a projecting release tab 78 positioned so that, as the slider 76 moves towards mandrel flange 74, release tab 78 bears on locking lever 72 and lifts it clear of the mandrel flange, freeing the flange, and hence mandrel 22 to be displaced by further motion of slider 76. This mechanism is shown highly schematically, and without detail of the spring or springs and the cutting element flange. It will however be clear that a single-slider implementation including a mandrel locking mechanism which is released by the initial motion of a manually-operated slider can readily be implemented by a person having ordinary skill in the art on the basis of the teachings of the present invention.

Turning now to a fourth aspect of the present invention, which may be used to advantage alone or in combination with any and all of the other aspects of the present invention described above, this relates to an "over-the-wire" (OTW) implementation of a knot pusher and/or suture cutter which is guided to the desired location by a guidewire 82. Many minimally-invasive surgical procedures are performed using a guidewire to guide various tools or implants to the target location. In certain cases, when a guidewire is already in place from a previous stage of a procedure, it may be highly advantageous to achieve precise guidance of a knot pusher to the target location by employing the guidewire to guide the knot pusher.

According to this aspect of the present invention, knot pusher 10' is formed with a guidewire lumen 80, extending along, and typically within, tubular suture holder 12, and preferably extending from end-to-end of the entire device. The knot pusher may include any, all or none of the features described above in relation to the various other aspects of the present invention. By way of a non-limiting example, FIGS. 23A-25D illustrate how the OTW implementation can be integrated with the other features described above by implementing a guidewire lumen along the lower part of tubular suture holder 12.

In order to facilitate manipulation of the device for inserting sutures into the suture gate, this may advantageously be done before the guidewire is introduced into lumen 80.

It will be appreciated that the above descriptions are intended only to serve as examples, and that many other embodiments are possible within the scope of the present invention as defined in the appended claims.

What is claimed is:

1. A knot pusher for pushing a knot along a suture, the knot pusher comprising:

(a) a tubular suture holder having a tubular wall defining an internal bore having a central longitudinal axis and terminating at a distal tip, said tubular suture holder having a suture-receiving slot formed through said tubular wall and extending proximally from said distal tip so that a segment of a suture can be loaded via said suture-receiving slot into said internal bore with a continuation of the suture emerging from said distal tip; and (b) a mandrel axially displaceable within said internal bore, said mandrel biased from a retracted position, in which said suture-receiving slot allows loading of a segment of a suture via said suture-receiving slot into said internal bore with a continuation of the suture emerging from said distal tip, towards an advanced position in which said mandrel obstructs a distal portion of said suture-receiving slot so as to entrap the segment of the suture within a part of said internal bore with the continuations of the suture extending from said distal tip and from a proximal portion of said suture-receiving slot, said mandrel defining a channel within said part of said internal bore so as to allow sliding of said suture along said channel, wherein said suture-receiving slot includes:

(i) a distal slot portion, adjacent to said distal tip, formed with a first edge and a second edge separated by a first width, said first width subtending an angle to the central longitudinal axis of less than 30 degrees, (ii) a first transition region starting at a first distance from said distal tip at which said first edge is shaped so as to diverge from said second edge and said second edge extends in an axial direction, and (iii) a second transition region starting at a second distance from said distal tip, said second distance being greater than said first distance, at which said second edge diverges from the axial direction away from said first edge, said first edge in said first transition region and said second edge in said second transition region defining at least part of an oblique groove crossing said tubular wall for receiving a suture.

2. The knot pusher of claim 1, wherein said oblique groove corresponds to an opening through said tubular wall the angular extremities of which subtend a groove angle of between 120 degrees and 240 degrees about the central longitudinal axis, and wherein an angular position of said distal slot portion is angularly spaced away from the ends of said oblique groove by at least about 20 degrees.

3. The knot pusher of claim 1, wherein a maximum depth of said oblique groove defines a base line of said oblique groove, and wherein a base plane of said oblique groove is defined as a plane containing said base line and parallel to said central axis, said second edge at a beginning of said second transition region providing a suture-capturing prominence, said suture-capturing prominence being at a height X from said base plane, where X is larger than said first width.

4. The knot pusher of claim 3, wherein height X is at least 30% of a radius of said tubular wall of said tubular suture holder.

5. The knot pusher of claim 1, wherein said distal tip of said tubular suture holder is formed with an end closure closing a majority of an area of said internal bore, said end closure including a radial slot contiguous with said distal slot portion of said suture-receiving slot, said radial slot terminating at a retaining aperture having a lateral dimension that is greater than said first width.

6. The knot pusher of claim 1, wherein said mandrel terminates in a least one projecting finger, said projecting finger having a cross-sectional area that is less than half of a cross-sectional area of said mandrel proximal to said projecting finger, said projecting finger being deployed such that, when a suture is trapped by said mandrel in said suture-receiving slot, tension in the suture tending to retract said mandrel towards said retracted position engages said suture with said projecting finger so as to inhibit release of the suture and to apply force to the suture to return the suture towards said distal tip.

7. The knot pusher of claim 1, further comprising an axially-displaceable cutting element, external or internal to said tubular suture holder, and selectively displaceable in a distal direction to cut a suture exiting via a proximal portion of said suture-receiving slot.

8. The knot pusher of claim 7, further comprising a handle supporting said tubular suture holder, said handle having a manually operable slider arrangement and an associated spring arrangement including at least one spring, said manually operable slider arrangement configured such that an axial force applied to said slider arrangement in a first axial direction acts against said spring arrangement to displace said mandrel from said advanced position to said retracted position and an axial force applied to said slider arrangement in a second axial direction opposite to said first axial direction acts against said spring arrangement to displace said cutting element to cut a suture exiting via a proximal portion of said suture-receiving slot, wherein said slider arrangement is locked by a locking configuration against displacement in said first axial direction, and wherein a release element of said slider arrangement is configured such that an initial displacement of said release element in said first axial direction is effective to unlock said locking configuration prior to displacement of said mandrel.

9. A knot pusher for pushing a knot along a suture, the knot pusher comprising:

(a) a tubular suture holder having a tubular wall defining an internal bore having a central longitudinal axis and terminating at a distal tip, said tubular suture holder having a suture-receiving slot formed through said tubular wall and extending proximally from said distal tip, said suture-receiving slot including a distal slot portion, adjacent to said distal tip, formed with a first edge and a second edge separated by a first width, and an oblique groove, proximal to and contiguous with said distal slot portion, having a width greater than said first width, for receiving a suture; and (b) a mandrel axially displaceable within said internal bore, said mandrel biased to an advanced position in which said mandrel obstructs a distal portion of said suture-receiving slot so as to slidingly-entrap a suture entering said internal bore at said distal tip and exiting via said oblique groove, said mandrel being retractable to a retracted position in which said suture-receiving slot is open to receive a suture, wherein said mandrel terminates in a least one projecting finger, said projecting finger having a cross-sectional area that is less than half of a cross-sectional area of said mandrel proximal to said projecting finger, said projecting finger being deployed such that, when a suture is trapped by said mandrel in said suture-receiving slot, tension in the suture tending to retract said mandrel towards said retracted position engages said suture with said projecting finger so as to inhibit release of the suture and to apply force to the suture to return the suture towards said distal tip.

10. A knot pusher for pushing a knot along a suture, the knot pusher comprising:

(a) a tubular suture holder having a tubular wall defining an internal bore having a central longitudinal axis and terminating at a distal tip, said tubular suture holder having a suture-receiving slot formed through said tubular wall and extending proximally from said distal tip, said suture-receiving slot including a distal slot portion, adjacent to said distal tip, formed with a first edge and a second edge separated by a first width, and an oblique groove, proximal to and contiguous with said distal slot portion, having a width greater than said first width, for receiving a suture;

(b) a mandrel axially displaceable within said internal bore, said mandrel biased to an advanced position in which said mandrel obstructs a distal portion of said suture-receiving slot so as to slidingly-entrap a suture entering said internal bore at said distal tip and exiting via said oblique groove, said mandrel being retractable to a retracted position in which said suture-receiving slot is open to receive a suture;

(c) an axially-displaceable cutting element, external or internal to said tubular suture holder, and selectively displaceable in a distal direction to cut a suture exiting via a proximal portion of said suture-receiving slot; and (d) a handle supporting said tubular suture holder, said handle having a manually operable slider arrangement and an associated spring arrangement including at least one spring, said manually operable slider arrangement configured such that an axial force applied to said slider arrangement in a first axial direction acts against said spring arrangement to displace said mandrel from said advanced position to said retracted position and an axial force applied to said slider arrangement in a second axial direction opposite to said first axial direction acts against said spring arrangement to displace said cutting element to cut a suture exiting via a proximal portion of said suture-receiving slot, wherein said slider arrangement is locked by a locking configuration against displacement in said first axial direction, and wherein a release element of said slider arrangement is linked to said locking configuration such that an initial displacement of said release element in said first axial direction is effective to unlock said locking configuration prior to displacement of said mandrel.

* * * * *